United States Patent [19]

Felix et al.

[11] Patent Number: 4,517,119
[45] Date of Patent: May 14, 1985

[54] SYNTHESIS OF THYMOSIN $\alpha_1$

[75] Inventors: Arthur M. Felix, West Caldwell, N.J.; Dieter Gillessen, Pratteln; William Lergier, Kaiseraugst, both of Switzerland; Johannes A. Meienhofer, Upper Montclair, N.J.; Arnold Trzeciak, Schopfheim, Fed. Rep. of Germany

[73] Assignee: Hoffmann-La Roche Inc., Nutley, N.J.

[21] Appl. No.: 482,113

[22] Filed: Apr. 4, 1983

[51] Int. Cl.³ .............................................. C07C 103/52
[52] U.S. Cl. .............................................. 260/112.5 R
[58] Field of Search .................. 260/112.5 R; 424/177

[56] References Cited

U.S. PATENT DOCUMENTS

| 4,079,127 | 3/1978 | Goldstein et al. | 424/177 |
| 4,116,951 | 9/1978 | Wang | 260/112.5 R |
| 4,148,788 | 4/1979 | Wang | 260/112.5 R |
| 4,339,427 | 7/1982 | Goldstein et al. | 260/112.5 R |
| 4,353,821 | 10/1982 | Birr et al. | 260/112.5 R |

OTHER PUBLICATIONS

Birr et al., *Angew. Chem. Int. Ed. Engl.*, 18(5), 394–395 (1979).
Abiko et al., *Chem. Pharm. Bull.*, 30(5), 1776–1783 (1982).
Wang et al., *J. Am. Chem. Soc.*, 101(1), 253–254 (1979).

*Primary Examiner*—Delbert R. Phillips
*Assistant Examiner*—F. T. Moezie
*Attorney, Agent, or Firm*—Jon S. Saxe; Bernard S. Leon; George M. Gould

[57] ABSTRACT

An improved solution phase synthesis of thymosin $\alpha_1$ and proceeding through novel intermediates is disclosed.

2 Claims, 7 Drawing Figures

SYNTHESIS OF FRAGMENT II

SYNTHESIS OF FRAGMENT III

FIG. 5

SYNTHESIS OF FRAGMENT IV

III

SYNTHESIS OF THYMOSIN α₁

BACKGROUND OF THE INVENTION

The isolation of biologically important peptides from the thymus gland has been studied extensively in the last few years. Several peptides have been shown to play certain roles in T-cell maturation. Thymosin $\alpha_1$, a highly acidic acetyl octacosapeptide isolated from calf thymus gland and characterized by sequence analysis has been reported to exhibit biological activities involved in the development of thymus-dependent lymphocytes (T-cells).

The isolation and characterization of thymosin $\alpha_1$ was disclosed in U.S. Pat. No. 4,079,127. Synthesis of this peptide by solution and solid phase procedures was disclosed in U.S. Pat. No. 4,148,788.

An alternate solution phase synthesis for thymosin $\alpha_1$ employing a different synthetic strategy was described by Birr and Stollenwerk, Angew. Chem. Int. Ed. Engl. 18, 394 (1979).

BRIEF DESCRIPTION OF THE INVENTION

The present invention relates to an improved process for the preparation of thymosin $\alpha_1$. This process involves the use of solution phase peptide synthetic techniques to accomplish the synthesis of several protected fragment precursors which in turn are used to prepare a key intermediate, the protected carboxy terminus docosapeptide.

More specifically, the invention relates to a compound of the formula Z-Thr(tBu)-Ser(tBu)-Ser(tBu)-Glu(OtBu)-Ile-Thr(tBu)-Thr(tBu)-Lys(Boc)-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn-OtBu (VII), wherein Z is benzyloxycarbonyl, Boc is t-butyloxycarbonyl and tBu is t-butyl, as well as to the corresponding compound with a deblocked amino terminus of the formula H-Thr(tBu)-Ser(tBu)-Ser(tBu)-Glu(OtBu)-Ile-Thr(tBu)-Thr(tBu)-Lys(Boc)-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn-OtBu (VIII), wherein Boc is t-butyloxycarbonyl and tBu is t-butyl.

The invention involves the use of tert-butyl as side chain protecting groups. This allows use of mild acid hydrolysis of the protective groups from the protected precursor compound to the desired end product and thereby avoids the use of final deprotection with very strong acid such as liquid HF which can cause extensive degradation of the product. A further aspect of the invention is the use of a halogenated hydrocarbon as a solvent in the coupling reaction of the side chain protected acetylated N-terminal hexapeptide with the protected carboxy terminus docosapeptide. The instant process thus provides a highly efficient procedure for producing the desired thymosin $\alpha_1$ in higher yield than heretofore been possible.

DESCRIPTION OF THE INVENTION

The process for the preparation of thymosin $\alpha_1$ in accordance with the present invention comprises coupling the compound of formula VIII with the compound of formula Ac-Ser(tBu)-Asp(OtBu)-Ala-Ala-Val-Asp(OtBu)-OH, wherein Ac is acetyl and tBu is t-butyl, and treating the resulting protected thymosin $\alpha_1$ with trifluoroacetic acid to remove the protecting groups.

In a further aspect of the present invention the preparation of protected thymosin $\alpha_1$ of the formula Ac-Ser(tBu)-Asp(OtBu)-Ala-Ala-Val-Asp(OtBu)-Thr(tBu)-Ser(tBu)-Ser(tBu)-Glu(OtBu)-Ile-Thr(tBu)-Thr(tBu)-Lys(Boc)-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn-OtBu, wherein Ac is acetyl, tBu is t-butyl and Boc is t-butyloxycarbonyl, is achieved by coupling Ac-Ser(tBu)-Asp(OtBu)-Ala-Ala-Val-Asp(OtBu)-OH with the compound of formula VIII in a halogenated hydrocarbon solvent in the presence of a conventional coupling reagent. Preferred halohydrocarbons useful in this reaction are chloroform, dichloromethane and mixtures of these two solvents. The high yield of protected thymosin $\alpha_1$ obtained in accordance with the coupling reaction is surprising in view of a statement in the literature (Birr et al. in Peptides, Structure and Biological Function, Proceedings of the Sixth American Peptide Symposium, Ed. E. Gross and J. Meienhofer, Pierce Chemical Company, Rockford, Ill., 1979, p. 399–400) that the N-terminal acetyl-hexapeptide is only slightly soluble in dichloromethane.

Figure 1:
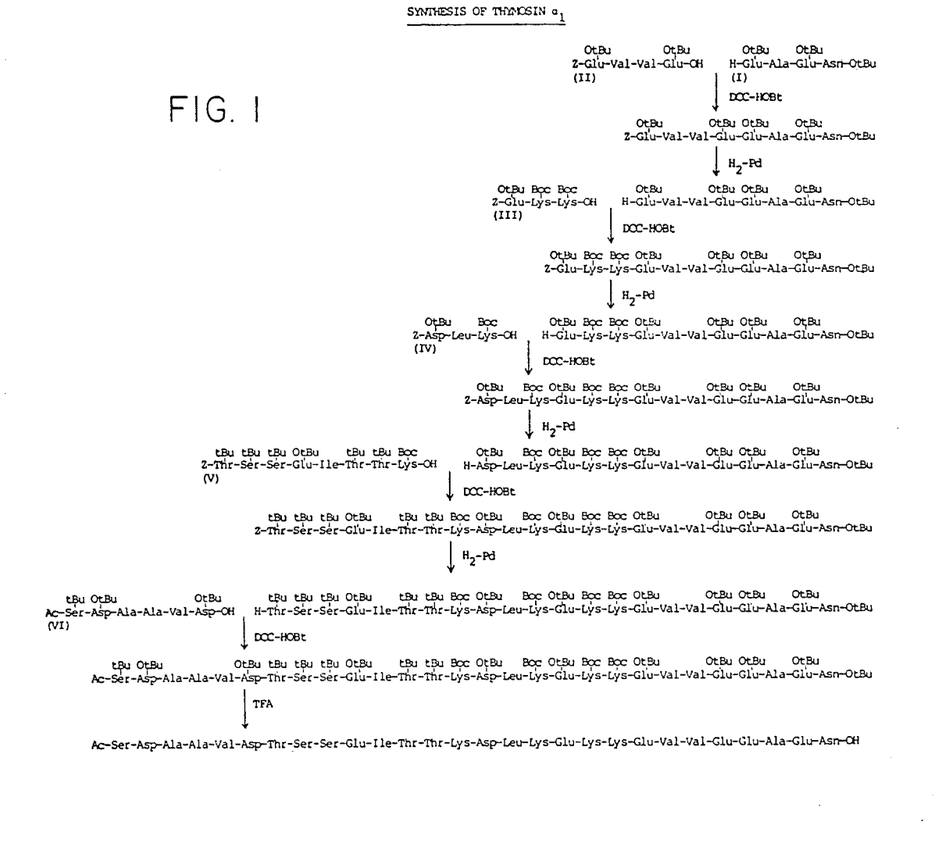
FIG. 1 sets forth the synthesis strategy for thymosin $\alpha_1$ from six protected peptide fragments (I–VI).

As seen from the synthetic strategy set forth in FIG. 1 the procedure utilized for the synthesis of thymosin $\alpha_1$ in accordance with the present invention required the synthesis of 6 fragments (I–VI). The synthetic approaches to the 6 fragments are outlined in FIGS. 2–7 respectively. Fragment VI has also been described by Birr et al. (e.g. Angew. Chem. 91, 422 [1979]).

Figure 2:
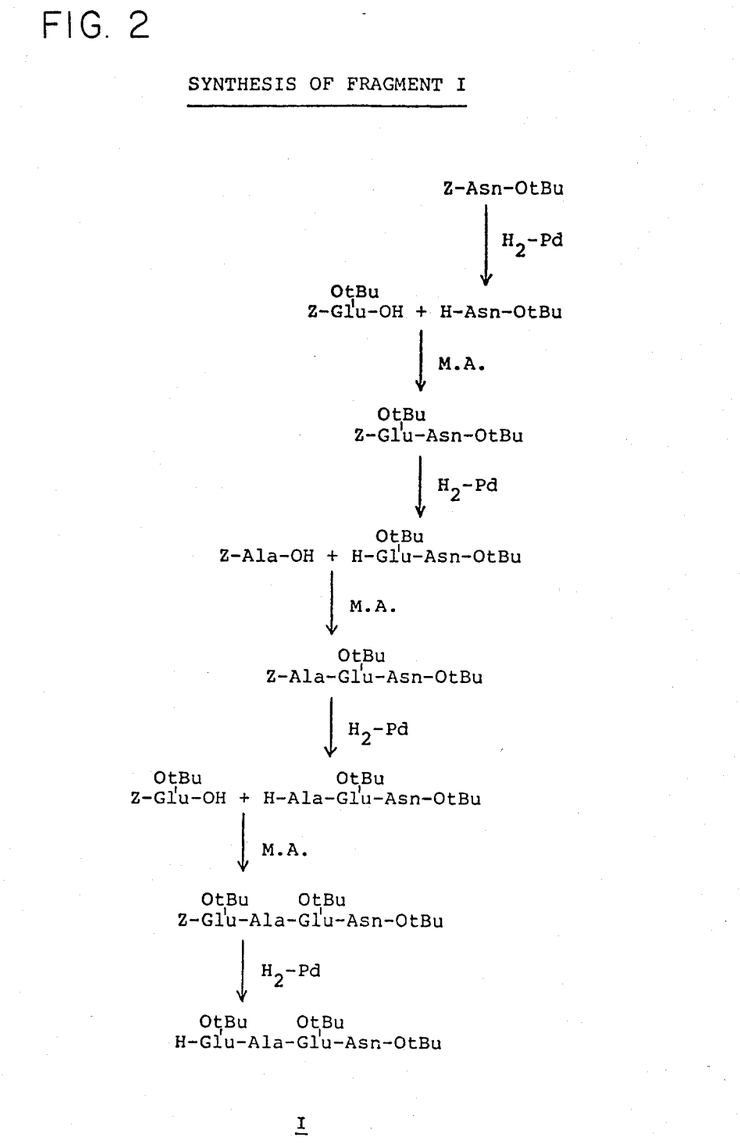
FIG. 2 sets forth the procedure used to synthesize fragment I.

Fragment I was prepared by stepwise chain elongation using the mixed anhydride procedure at −15° C. with careful temperature control. As seen in the scheme of FIG. 2 mixed anhydride (M.A.) coupling (isobutylchloroformate) of Z-Glu(OtBu)-OH with H-Asn-OtBu provided Z-Glu(OtBu)-Asn-OtBu. Catalytic hydrogenation (10% Pd-C) of this compound cleaved the N-terminal protective group and the dipeptide was coupled to Z-Ala-OH using mixed anhydride coupling to give Z-Ala-Glu (OtBu)-Asn-OtBu. The N-terminal was again deprotected by catalytic hydrogenation and the tripeptide coupled with Z-Glu(OtBu)-OH to give the protected tetrapeptide Z-Glu(OtBu)-Ala-Glu(OtBu)-Asn-OtBu which is deblocked by catalytic hydrogenation to provide the desired protected tetrapeptide (1).

Figure 3:
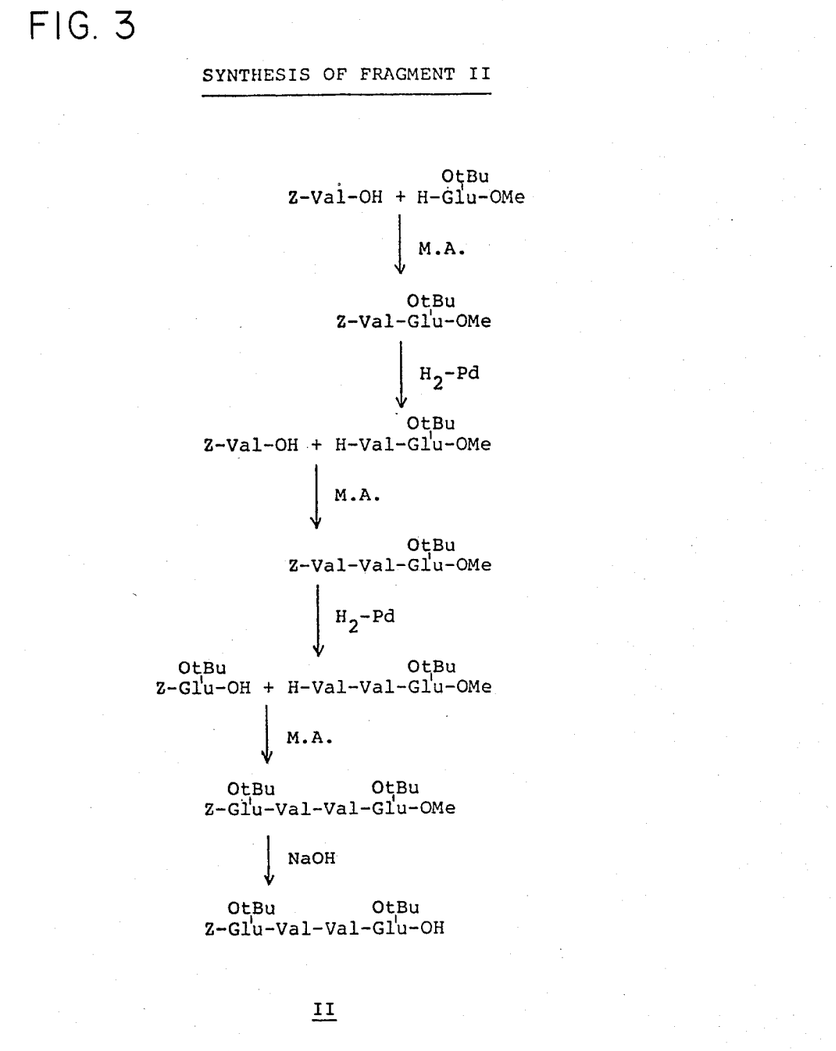
FIG. 3 sets forth the procedure used to synthesize fragment II.

The synthesis of fragment II is depicted in FIG. 3. Again all three coupling reactions were carried out by the mixed anhydride method. Thus HCL.H-Glu(OtBu)-OMe was converted to Z-Val-Glu(OtBu)-OMe, which after catalytic hydrogenation for 25 hours the resulting intermediate H-Val-Glu(OtBu)-OMe was immediately coupled (mixed anhydride) with Z-Val-OH. The resultant protected tripeptide Z-Val-Val-Glu(OtBu)-OMe was then catalytically hydrogenated to produce the corresponding N-terminal free peptide which was coupled (mixed anhydride) with Z-Glu(OtBu)-OH. The resulting protected tetrapeptide was then base saponified with 1N NaOH in DMF to provide fragment II.

Figures 4, 5:
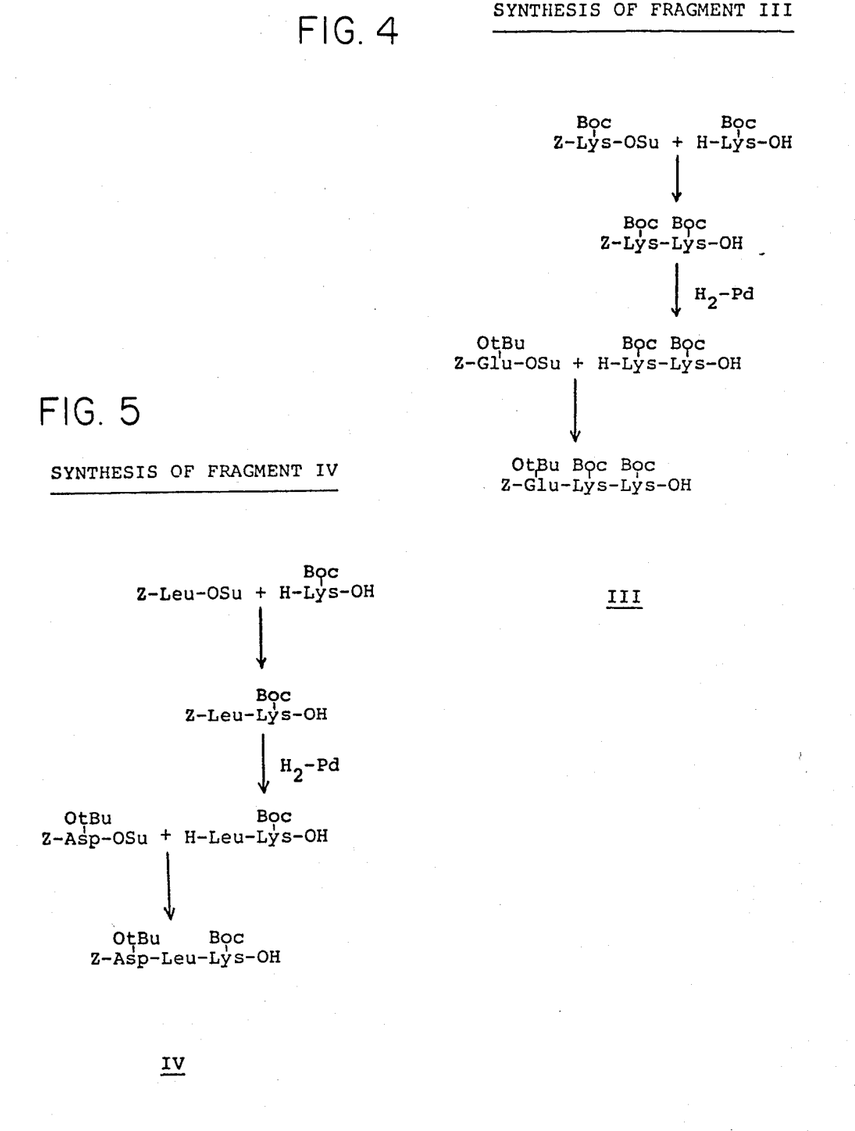
FIG. 4 sets forth the procedure used to synthesize fragment III.
FIG. 5 sets forth the procedure used to synthesize fragment IV.

In FIG. 4, the synthesis of fragment III is shown. Coupling of Z-Lys(Boc)-OSu with H-Lys(Boc)-OH gave Z-Lys(Boc)-Lys(Boc)-OH as the DCHA salt. Conversion to the free acid using $H_2SO_4$ in ether was followed by catalytic hydrogenation (5% Pd-BaSO$_4$) and coupling with Z-Glu(OtBu)-OSu to yield the desired fragment III Z-Glu(OtBu)-Lys(Boc)-Lys(Boc)-OH.

The scheme shown in FIG. 5 describes the preparation of fragment IV. Conversion of Z-Leu-OH to Z-Leu-OSu and Z-Asp(OtBu)-OH to Z-Asp(OtBu)-OSu was carried out in a manner known per se using DCC and HOSu. Coupling of Z-Leu-OSu with H-Lys(Boc)-OH provided Z-Leu-Lys(Boc)-OH as the DCHA salt. Conversion to the free amino terminus by catalytic hydrogenolysis (Pd-BaSO$_4$) gave H-Leu-Lys(Boc)-OH. Final coupling of H-Leu-Lys(Boc)-OH with Z-Asp-(OtBu)-OSu gave Fragment IV.

Figure 6:
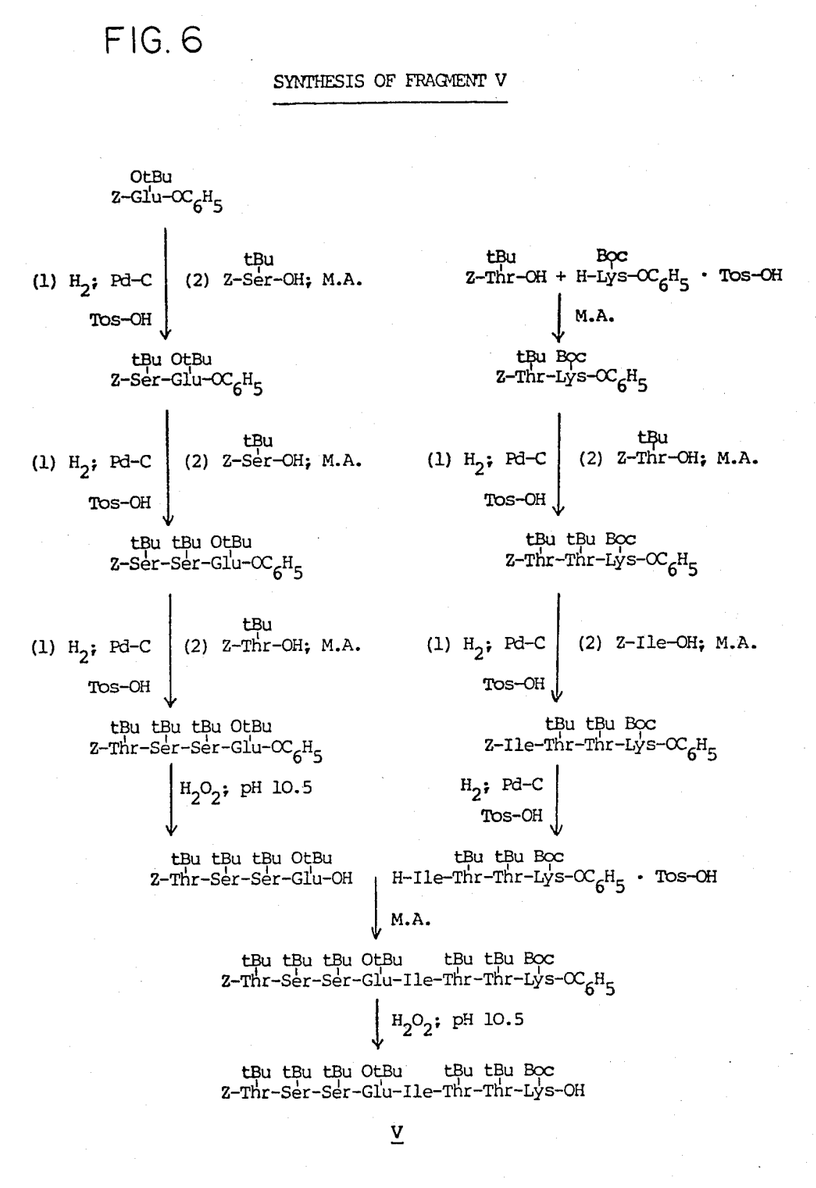
FIG. 6 sets forth the procedure used to synthesize fragment V.

FIG. 6 shows the procedure used for preparing Fragment V. Z-Lys(Boc)-OH was esterified with phenol and the amino terminal deblocked by catalytic hydrogenation over 10% Pd-C in the presence of TosOH to form H-Lys(Boc)-OC$_6$H$_5$.TosOH. After coupling (mixed anhydride) with Z-Thr (tBu)-OH the resulting dipeptide is catalytically deblocked and coupled with Z-Thr(tBu)-OH to provide the tripeptide Z-Thr (tBu)-Thr(tBu)-Lys(Boc)-OC$_6$H$_5$. After another cycle of catalytic deblocking and coupling with Z-Ile-OH (mixed anhydride), the resulting protected tetrapeptide ester is again deblocked at the amino terminus by catalytic hydrogenation in the presence of TosOH to yield H-Ile-Thr (tBu)-Thr(tBu)-Lys(Boc)-OC$_6$H$_5$.Tos-OH.

The esterification of Z-Glu(OtBu)-OH with phenol is carried out under conventional conditions and the resulting phenyl ester, after catalytic (Pd-C) deblocking is coupled (mixed anhydride) with Z-Ser(tBu)-OH to provide the dipeptide Z-Ser(tBu)-Glu(OtBu)-OC$_6$H$_5$. Two additional cycles of deblocking and mixed anhydride coupling with Z-Ser(tBu)-OH and Z-Thr(tBu)-OH respectively provided the protected tetrapeptide Z-Thr(tBu)-Ser(tBu)-Ser(tBu)-Glu(OtBu)-OC$_6$H$_5$. Saponification with dilute, basic hydrogen peroxide gave the corresponding free carboxyl terminus tetrapeptide which upon mixed anhydride coupling with the above side chain protected tetrapeptide ester tosyl salt and saponification with dilute, basic hydrogen peroxide provided the desired octapeptide fragment V.

Figure 7:
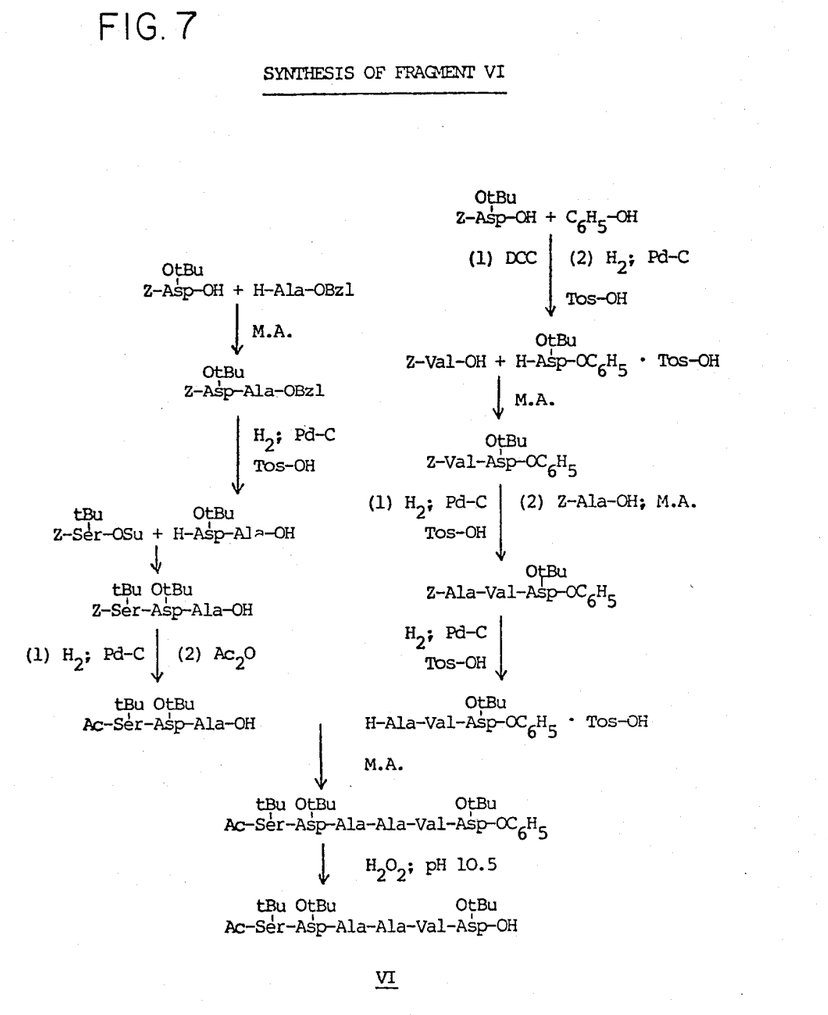
FIG. 7 sets forth the procedure used to synthesize fragment VI.

Construction of the amino terminal fragment, Fragment VI, is set forth in FIG. 7. Mixed anhydride coupling of Z-Asp(OtBu)-OH with H-Ala-OBzl produced the protected dipeptide which was deblocked by catalytic hydrogenation with Pd-C in the presence of TosOH. The resulting deblocked dipeptide in the form of the tosyl salt was then coupled to Z-Ser(tBu)-OSu to provide the protected tripeptide Z-Ser(tBu)-Asp(OtBu)-Ala OH. After deblocking by catalytic hydrogenation the resulting tripeptide was treated with acetic anhydride to provide the blocked N-terminal acetyl tripeptide. This blocked tripeptide, Ac-Ser (tBu)-Asp(OtBu)-Ala-OH, was then coupled to H-Ala-Val-Asp(OtBu)-OC$_6$H$_5$.TosOH (mixed anhydride) to yield the blocked hexapeptide Ac-Ser(tBu)-Asp(OtBu)-Ala-Ala-Val-Asp(OtBu)-OC$_6$H$_5$ which after saponification with dilute, basic hydrogen peroxide provided Fragment VI.

The tripeptide ester tosyl salt H-Ala-Val-Asp(OtBu)-OC$_6$H$_5$.TosOH was obtained by reacting Z-Val-OH with H-Asp(OtBu)-OC$_6$H$_5$.TosOH (mixed anhydride), deblocking the resulting dipeptide by catalytic hydrogenation with Pd-C, coupling with Z-Ala-OH (mixed anhydride) and again deblocking by catalytic hydrogenation.

The following Examples illustrate but do not limit the instant invention.

EXAMPLES

Materials

All amino acid derivatives were of the L-configuration unless otherwise stated. Dimethylformamide (reagent grade, Matheson Coleman and Bell) was distilled from ninhydrin at reduced pressure and stored over molecular sieve. Tetrahydrofuran (reagent grade, Matheson Coleman and Bell) was distilled from LiAlH$_4$. Trifluoroacetic acid and N-Methylmorpholine (Chemical Dynamics) were sequenal grade purity. Trifluoroethanol (Aldrich Chemical Co.) was distilled at atmospheric pressure prior to use. Dimethysulfoxide (distilled in glass) and pyridine (distilled in glass) were purchased from Burdick and Jackson. Hydroxybenzotriazole and triethylamine (sequenal grade purity) were purchased from Pierce Chemical Co. The catalysts for hydrogenation were purchased from the Englehard Co. Catalytic hydrogenations were carried out in a Vibromixer apparatus as previously described, Meienhofer, Chima 16, 385 (1962). All other solvents were of reagent grade and used without further purification.

Methods

TLC was carried out on silica gel G plates (Analtech, Inc.) and developed with cholorine-TDM. Typically, 2 mg of sample was dissolved in 150 µl of solvent and 3 µl (50 ug) applied to the tlc plate.

Melting points were determined on the Hoover apparatus (with correction) or on a Reichert hot stage apparatus (without correction). Infra-red and nmr spectra were measured and found to be compatible for all new products synthesized. Optical rotations were measured in a jacketed 1-dm cell on a Perkin Elmer Model 141 Polarimeter. Electrophoresis was carried out on the Camag HVE apparatus using S & S 2040-B paper and silica gel G plates (see above) and developed with ninhydrin.

The CD spectrum was measured on a Jasco ORD-UV/5 spectro-polarimeter at ambient temperature in 0.05M phosphate buffer at pH 7.4 using a concentration of $2 \times 10^{-4}$M and path lengths of 0.001 dm to 0.10 dm. The spectrum was qualitatively similar to that reported for thymosin $\alpha_1$. The nmr spectra of the 2 peptide fragments, 8 and 12, were measured on a Varian XL-100 Spectrometer. The nmr spectrum of thymosin $\alpha_1$ was measured on a Varian XL-200 Spectrometer. Peptide mapping was carried out by digesting thymosin $\alpha_1$ with trypsin-TPCK at pH 8.0. The fragment migration patterns on tlc plates (see above) were found to be identical to the reference standard. Isoelectric focusing was carried out using a DC LKB-2103 power supply and LKB 2177 multiphor. The protein precipitin bands and coomasie staining was identical to the reference standard.

High performance liquid chromatography was performed on an LDC Constametric IIG equipped with a gradient master and Spectromonitor III UV detector (206 nm). A Waters Bondapack $C_{18}$ with a pre-column of Copell ODS pellicular packing (Whatman) was used. The column was equilibrated with 8% $CH_3CN$ in $H_2O$ containing 0.022% TFA. The sample in $H_2O$ (∼1 μg/μL) was adjusted to pH ∼8 with 0.1N $NH_4OH$ and applied onto the column and eluted with 0.022% TFA-$H_2O$ and a linear gradient of 0.022% TFA-$CH_3CN$ was introduced to bring the $CH_3CN$ concentration to 22% over a period of 30 min (flow rate 2 mL/min.).

EXAMPLE 1

Synthesis of Fragment I (γ-t-Butyl-L-glutamyl-L-alanyl-γ-t-butyl-L-glutamyl-L-asparagine-t-butyl ester)

(a) N-Benzyloxycarbonyl-γ-t-butyl-L-glutamyl-L-asparagine t-butyl ester

A solution of Z-Glu(OtBu)-OH (212.5 g, 0.63 mol, 1.05 eq.) in DMF (400 mL) was placed in a 2-l 3-neck creased round bottom flask fitted with a thermometer, mechanical stirrer, dropping funnel and immersed in a dry ice-acetone bath at −15°. The reaction was carried out under an atmosphere of $N_2$, cooled to −15° and precooled (−20°) N-methylmorpholine (95.6 g, 0.945 mol, 1.575 eq.) added. After stirring for 4 min at −15°, the reaction mixture was cooled to −25° and precooled (−20°) isobutylchloroformate (86.0 g, 0.63 mol, 1.05 eq.) added portionwise over a 2 minute period (temperature must not exceed −15°). The reaction mixture stirred for an additional 4 min at −25° and a precooled (−20°) solution of H-Asn-OtBu (112.9 g, 0.60 mol, 1 eq.) in DMF (440 mL)-$CH_2Cl_2$ (40 mL) added as rapidly as possible while the temperature was maintained at −15° to −20°. After the addition was complete the reaction mixture was stirred at −15° for 30 min and at 25° for 2.5 h. The reaction mixture was filtered and the filter cake washed with DMF (2×50 mL). The filtrate was evaporated in vacuo and the resultant syrup dissolved in $CH_2Cl_2$ (2.5 l) and washed with 10% $NaHCO_3$ (2×450 mL), sat'd. NaCl (1×400 mL), 10% citric acid (3×450 mL), sat'd. NaCl (1×400 mL). It was dried ($MgSO_4$), filtered (celite) and evaporated to dryness to give a syrup which solidified on standing mp 136°–140°. Crystallization from ispropanol (1.1 l): ligroin (3 l) gave 269.9 g (88.6%) of white crystals; mp 143°–145°; $[\alpha]_D^{25} -19.06°$ (c 1, MeOH); $R_f$ 0.20 ($CHCl_3$:MeOH:AcOH; 80-2-0.4); $R_f$ 0.80 ($CHCl_3$:MeOH:AcOH; 80-10-0.4).

Anal. Calc. for $C_{25}H_{37}N_3O_8$(507.6): C, 59.16; H, 7.35; N, 8.28. Found: C, 59.24; H, 7.34; N, 8.40.

(b) γ-t-Butyl-L-glutamyl-L-asparagine t-butyl ester

A solution of Z-Glu(OtBu)-Asn-OtBu (40.0 g, 0.079 mol) in MeOH (250 mL) containing 10% Pd-C (5.0 g) was reduced in a Parr hydrogenator[a] until the theoretical amount of $H_2$ was taken up (and no further uptake of $H_2$ was observed). The reaction mixture was filtered through celite (topped with a bed of $MgSO_4$) and evaporated to dryness. A total of 590 g of Z-Glu(OtBu)-Asn-OtBu was reduced and the combined material crystallized by treatment of the residue with MeOH. Evaporation of solvent resulted in the isolation of 397 g (91.4%) of white needles; mp 117°–119°; $[\alpha]_D^{25} -4.98°$ (c 1, MeOH); $R_f$ 0.25 ($CHCl_3$:MeOH:AcOH; 85-10-5).

Anal. Calc. for $C_{17}H_{31}N_3O_6$ (373.5): C, 54.68; H, 8.37; N, 11.25. Found: C, 55.06; H, 8.76; N, 11.12.

(a) Alternatively, the Vibromixer apparatus may be used for larger scale hydrogenations.

(c) N-Benzyloxycarbonyl-L-alanyl-γ-t-butyl-L-glutamyl-L-asparagine t-butyl ester A solution of Z-Ala-OH (118.5 g, 0.53 mol, 1.05 eq.) in DMF (400 mL) was placed in a 2-l 3-neck creased round bottom flask fitted with a thermometer, mechanical stirrer, dropping funnel and immersed in a dry ice-acetone bath at −15°. The reaction was carried out under an atmosphere of $N_2$, cooled to −15° and precooled (−20°) N-methylmorpholine (80.9 g, 0.80 mol, 1.58 eq.) added. After stirring for 4 min at −15°, the reaction mixture was cooled to −25° and precooled (−20°) isobutylchloroformate (72.5 g, 0.53 mol, 1.05 eq.) added portionwise over a 2 min period (temperature must not exceed −15°). The reaction mixture stirred for an additional 4 min at −25° and a precooled (−20°) solution of H-Glu(OtBu)-Asn-OtBu (189 g, 0.506 mol) in DMF (350 mL)-$CH_2Cl_2$ (150 mL) added as rapidly as possible while maintaining −15° to −20° (4 minutes). After the addition was complete the reaction mixture was stirred at −15° for 30 min and at 25° for 3 h. The reaction mixture was filtered and the filter cake washed with DMF (2×50 mL). The filtrate was evaporated in vacuo and the resultant syrup immediately poured into $H_2O$ (3.5 l). The suspension was stirred for 18 h and the product collected by filtration and washed with $H_2O$ (2×500 mL) and dried in vacuo. A total of 575.6 g (98.3%) was prepared in 2 batches. Recrystallization from EtOH (3.5 l):$H_2O$ (5 l) gave 533.4 g (91.1%); mp 174°–176°; $[\alpha]_D^{25} -35.48°$ (c 1, MeOH); $R_f$ 0.25 ($CHCl_3$:MeOH:AcOH; 80-20-5).

Anal. Calc. for $C_{28}H_{42}N_4O_9$ (578.66): C, 58.12; H, 7.32; N, 9.68. Found: C, 57.81; H, 7.37; N, 9.44.

(d) L-Alanyl-γ-t-butyl-L-glutamyl-L-asparagine t-butyl ester

A solution of Z-Ala-Glu(OtBu)-Asn-OtBu (40.0 g, 0.069 mol) in MeOH (200 mL) containing 10% Pd-C (5.0 g) was hydrogenated in a Parr hydrogenator[a] until the theoretical amount of $H_2$ was taken up (and no further uptake of $H_2$ was observed). The reaction mixture was filtered through celite (topped with a bed of $MgSO_4$) and evaporated to dryness. A total of 570.9 g of Z-Ala-Glu(OtBu)-Asn-OtBu was reduced and the combined material triturated with ether. The resultant while solid was filtered and dried in vacuo to give 427.6 g (97.5%); mp 112°–118°; $[\alpha]_D^{25} -18.96°$ (c 1, MeOH); $R_f$ 0.15 ($CHCl_3$:MeOH:AcOH; 80-20-5).

Anal. Calc. for $C_{20}H_{36}N_4O_7$ (444.53): C, 54.04; H, 8.16; N, 12.60. Found: C, 54.27; H, 7.98; N, 12.52.

(a) Alternatively, the Vibromixer apparatus may be used for larger scale hydrogenations.

(e) N-Benzyloxycarbonyl-γ-t-butyl-L-glutamyl-L-alanyl-γ-t-butyl-L-glutamyl-L-asparagine t-butyl ester A solution of Z-Glu(OtBu)-OH (269.9 g, 0.80 mol, 1.04 eq.) in DMF (500 mL) was placed in a 3-l 3-neck creased round bottom flask fitted with a thermometer, mechanical stirrer, dropping funnel and immersed in a dry ice-acetone bath at −15°. The reaction was carried out under an atmosphere of $N_2$, cooled to −15° and precooled (−20°) N-methylmorpholine (125 g, 1.24 mol, 1.6 eq.) added. After stirring for 4 min at −15°, the reaction mixture was cooled to −35° and precooled (−20°) isobutylchloroformate (109.3 g, 0.80 mol, 1.04 eq.) added portionwise over a 3 min period (temperature must not exceed −15°). The reaction mixture stirred for an additional 4 min at −15°, cooled to −35° and a precooled (−20°) solution of H-Ala-Glu(OtBu)-Asn-OtBu (341.4 g, 0.768 mol, 1 eq) in DMF (750 mL) added as rapidly as possible while maintaining −15° to −20°. After the addition was complete the reaction mixture was stirred at −15° for 30 min and at 25° for 2½ h. The reaction mixture was slowly poured into H$_2$O (9.5 l) while stirring rapidly and stirred for 2 h. The product was collected by filtration and washed with H$_2$O (until the filtrate was free of Cl−) and dried in vacuo. A total of 558.7 g was obtained. Recrystallization from CH$_3$CN (refluxing required) gave 525.5 g (89.6%) of white solid; mp 212°–214°; $[\alpha]_D^{25}$ −15.82° (c 1, DMF); R$_f$ 0.83 (CHCl$_3$:MeOH:AcOH; 85-10-5).

Anal. Calc. for C$_{37}$H$_{57}$N$_5$O$_{12}$ (763.89): C, 58.18; H, 7.52; N, 9.17. Found: C, 58.48; H, 7.56; N, 9.37.

(f)
γ-t-Butyl-L-glutamyl-L-alanyl-γ-t-butyl-L-glutamyl-L-asparagine t-butyl ester (I)

A suspension of Z-Glu(OtBu)-Ala-Glu(OtBu)-Asn-OtBu (147.3 g, 0.193 mol) in MeOH (1.6 L) containing 5% Pd-BaSO$_4$ (34.1 g) was hydrogenated in the Vibromixer apparatus for 3 h. The reaction mixture was filtered through celite and evaporated to 150 mL. Ether (1.4 L) was added and the resultant white solid was filtered and dried in vacuo. Yield: 103.1 g; second crop, 15.0 g (97.2%); mp 161°–164°; $[\alpha]_D^{25}$ −29.55° (c 1, MeOH); R$_f$ 0.70 (n-BuOH:AcOH:EtOAc:H$_2$O; 1-1-1-1); R$_f$ 0.26 (CHCl$_3$:MeOH:AcOH; 80-20-5).

Anal. Calc. for C$_{29}$H$_{51}$N$_5$O$_{10}$ (629.75): C, 55.31, H, 8.16; N, 11.12. Found: C, 55.05; H, 7.80; N, 11.29.

EXAMPLE 2

Synthesis of Fragment II
(N-Benzyloxycarbonyl-γ-t-butyl-L-glutamyl-L-valyl-L-valyl-γ-t-butyl-L-glutamic acid (a) N-Benzyloxycarbonyl-L-valyl-γ-t-butyl-L-glutamic acid methyl ester N-Benzyloxycarbonyl-L-valine (144 g, 0.58 mol, 1.2 eq) was dissolved in 400 ml freshly distilled THF and stirred mechanically in a 3-l 3-neck round bottom flask fitted with a thermometer and dropping funnel and immersed in a dry ice-alcohol bath at −15°. While stirring at −15°, N-methylmorpholine (55 ml, 0.58 mol, 1.2 eq) was added dropwise. The temperature was maintained at −15° and isobutylchloroformate (66.2 ml, 0.58 mol, 1.2 eq) was added dropwise over a 2 min period. The reaction mixture stirred for an additional 2 min at −15° and a precooled (−20°) solution of L-glutamic acid α-methyl ester γ-t-butyl ester.HCL (120.8 g, 0.48 mol) dissolved in 300 ml THF and 150 ml DMF was added dropwise with simultaneous addition of N-methylmorpholine (46 ml, 0.48 mol). [The addition took 6 min while maintaining the temperature below −15°.] The reaction mixture was stirred for 30 min at −15°, and for 3 h at 25°, evaporated in vacuo and the residue dissolved in EtOAc (900 ml) and washed with 10% NaHCO$_3$ (3×200 ml), 1M citric acid (3×200 ml) and satd. NaCl solution (1×200 ml). The aqueous washes were backwashed with EtOAc and the combined organic layers were dried over MgSO$_4$, filtered and concentrated to ~200 ml and pet. ether (1 l) added. The solid was collected and dried in vacuo(*) and the combined crops were recrystallized from CCl$_4$ (400 ml) pet. ether (1.2 l) to yield 168.5 g (78%) of white crystalline product; mp 66.5°–68°; R$_f$ 0.74 (n-BuOH:AcOH:EtOAc:H$_2$O; 1-1-1-1), R$_f$ 0.73 (CHCl$_3$:CH$_3$OH:AcOH; 80-5-1); $[\alpha]_D^{25}$ −28.91°, (c 1, MeOH). Anal. calc. for C$_{23}$H$_{24}$N$_2$O$_7$ (450.5): C, 61.32; H, 7.61; N, 6.22. Found: C, 61.23; H, 7.58; N, 6.01.

(*) A second crop was obtained from the mother liquor.

(b)
N-Benzyloxycarbonyl-L-valyl-L-valyl-γ-tert.butyl-L-glutamic acid α-methyl ester (A) N-Benzyloxycarbonyl-L-valyl-γ-tert.butyl-L-glutamic acid methyl ester (58.0 g, 128.8 mmol) was dissolved in DMF:THF (50 ml:160 ml), 5% Pd-BaSO$_4$ (12.8 g) added and hydrogenated in the Vibromixer apparatus for 2.5 h. The reaction mixture was filtered through celite, cooled to 0° and the resultant solution of L-valyl-γ-tert.butyl-L-glutamic acid metyl ester was placed in the freezer until used in the coupling stage below.(*)

(*)The intermediate must be coupled within several hours since it may undergo cyclization to the diketopiperazine. Retention of this intermediate at −30° will slow down this side reaction.

(B) N-Benzyloxycarbonyl-L-valine (38.8 g, 154.6 mmol, 1.2 eq) was dissolved in 45 ml freshly distilled THF in a 2-l 3-neck round bottom flask fitted with a thermometer, mechanical stirrer and dropping funnel and immersed in a dry ice-alcohol bath at −15°. While stirring at −15°, N-methylmorpholine (17.3 ml, 154.6 mmol) was added. This was followed by the addition of isobutylchloroformate (20.3 ml, 154.6 mmol) dropwise over a 2 min period. The reaction was stirred an additional 2 min at −15° and the precooled (−20°) solution of L-valyl-γ-tert.butyl-L-glutamic acid α-methyl ester (128.8 mmol from above) was added over a 2.7 min period. The reaction mixture was stirred at −15° for 30 min and at 25° for 17 h, evaporated in vacuo and the residue dissolved in CHCl$_3$ (600 ml) and washed with 10% NaHCO$_3$ (3×300 ml), satd. NaCl (1×300 ml), 1M citric acid (2×300 ml) and satd. NaCl (1×300 ml). The aqueous phases were backwashed with CHCl$_3$ and the combined organic layers dried over MgSO$_4$, filtered and evaporated in vacuo. The product was recrystallized from i-PrOH (4 l) to yield 41.6 g (59%) of white crystalline product; mp 203°–204°; R$_f$ 0.47 (CHCl$_3$:CH$_3$OH:AcOH; 80-2-0.4); R$_f$ 0.74 (CHCl$_3$:CH$_3$OH:AcOH; 80-5-1); $[\alpha]_D^{25}$ −7.40° (c 1, DMF). Anal. calc. for C$_{28}$H$_{43}$N$_3$O$_8$ (549.7): C, 61.18; H, 7.89; N, 7.64. Found: C, 61.43; H, 7.96; N, 7.41.

(c) L-Valyl-L-valyl-γ-tert.butyl-L-glutamic acid α-methyl ester

N-Benzyloxycarbonyl-L-valyl-L-valyl-γ-tert.butyl-L-glutamic acid α-methyl ester (19.5 g, 35.5 mmol) was dissolved in 250 ml DMF, 5% Pd/BaSO$_4$ (6 g) added and hydrogenated in the Vibromixer apparatus for 3 h. The reaction mixture was filtered through celite, washed with ~50 ml DMF, and evaporated in vacuo to yield 14.7 g (100%) of white solid; mp 126°–127°; R$_f$ 0.35 (CHCl$_3$:CH$_3$OH:AcOH; 80:10:5); $[\alpha]_D^{25}$ −41.05° (c 1, CH$_3$OH). Anal. calc. for C$_{20}$H$_{37}$N$_3$O$_6$ (415.5): C, 57.81; H, 8.98; N, 10.11. Found: C, 57.45; H, 8.96; N, 9.99.

(d)
N-Benzyloxycarbonyl-γ-t-butyl-L-glutamyl-L-valyl-L-valyl-γ-t-butyl-L-glutamic acid α-methyl ester Z-Glu(OtBu)-OH (14.4 g, 42.6 mmol, 1.2 eq) was dissolved in THF (120 ml) and placed in a 1-l, 3-neck round bottom flask fitted with a thermometer, mechanical stirrer and immersed in a dry ice-alcohol bath at −15°. N-Methylmorpholine (4.5 ml, 42.6 mmol, 1.2 eq) was added while stirring at −15° and the isobutyl-chloroformate (5.4 ml, 42.6 mmol, 1.2 eq) added dropwise over a 2 min period. The reaction mixture was stirred for 2 min at −15° and a precooled (0°) solution of H-Val-Val-Glu(OtBu)-OMe (14.7 g, 35.5 mmol) in THF:DMF (100 ml:20 ml) added dropwise over a 3 min period maintaining the temperature at −15°. Stirring proceeded at −15° for 30 min and at 25° for 18 h. The reaction mixture was evaporated to dryness, the white solid triturated with i-PrOH and filtered. A second crop of product was obtained from the mother liquor. The total amount of product was 23 g (88%); mp 210°–211°, $R_f$ 0.58 (CHCl$_3$:CH$_3$OH:AcOH; 80-2-0.4); $[\alpha]_D^{25}$ −22.53° (c 1, DMSO). Anal. calc. for $C_{37}H_{58}N_4O_{11}$ (734.9); C, 60.47; H, 7.96; N, 7.62. Found: C, 60.44; H, 7.95; N, 7.61.

(e)
N-Benzyloxycarbonyl-γ-t-butyl-L-glutamyl-L-valyl-L-valyl-γ-t-butyl-L-glutamic acid (II)

A solution of Z-Glu(OtBu)-Val-Val-Glu(OtBu)-OMe (46.5 g, 63.3 mmol) in DMF (550 mL) was treated with 1N NaOH (79.2 mL, 79.2 mmol, 1.25 eq.) and stirred magnetically for 3 h at 25°. It was cooled in an ice-bath and 1N HCl (190 mL) added followed by 1.25 L H$_2$O. The suspension was stirred for 2 h at 25° and the product collected by filtration, washed with 1 L H$_2$O and dried in vacuo. Yield: 41.9 g (91.8%). An analytical sample was recrystallized from MeOH-H$_2$O; mp 193°–196°; $[\alpha]_D^{25}$ −51.66° (c 1, MeOH); $R_f$ 0.34 (CHCl$_3$:MeOH:AcOH; 80-5-1). Anal. calc. for $C_{36}H_{56}N_4O_{11}$ (720.86): C, 59.98; H, 7.83; N, 7.77. Found: C, 59.91; H, 7.75; N, 7.85.

EXAMPLE 3

Synthesis of Fragment III
(N-Benzyloxycarbonyl-γ-t-butyl-L-glutamyl-N$^\epsilon$-t-butyloxycarbonyl-L-lysyl-N$^\epsilon$-t-butyloxycarbonyl-L-lysine)

(a)
N-Benzyloxycarbonyl-N$^\epsilon$-tert-butyloxycarbonyl-L-lysine N-hydroxysuccinimide ester Z-Lys(Boc)-OH.DCHA (454 g; 0.808 mol) was stirred magnetically in ethyl acetate:0.5N H$_2$SO$_4$ (1.5 l:2 l) until all the white solid was in solution. The organic layer was collected, dried over MgSO$_4$, filtered and evaporated. The resultant free acid was placed in a 3-l, 3-neck round bottom flask fitted with a thermometer, drying tube and mechanical stirrer and stirred at 0° in ethyl acetate:dioxane (400 mL:1000 mL). N-Hydroxysuccinimide (93.0 g; 0.808 mol) and DCC (166.6 g; 0.808 mol) were added and the reaction stirred at 0° for 1 h and 25° for 16 h. The reaction mixture was filtered and the filtrate evaporated in vacuo. The oily residue was dissolved in i-PrOH (500 mL) and petroleum ether (~700 mL) added, cooled to 4° for several hours, then filtered to yield 350.4 g (91%) product: mp 95°–97°; $R_f$ 0.81 (CHCl$_3$:CH$_3$OH:AcOH; 80:5:1); $[\alpha]_D^{25}$ −17.76° (c 2, Dioxane).

(b)
N$^\alpha$-Benzyloxycarbonyl-N$^\epsilon$-t-butyloxycarbonyl-L-lysyl-N$^\epsilon$-t-butyloxycarbonyl-L-lysine A solution of Z-Lys(Boc)-OSu (239 g; 0.5 mol) in DMF (1.5 l) was stirred at 0° in a 3-l, 3-neck round bottom flask fitted with a mechanical stirrer and thermometer. The H-Lys(Boc)-OH (123 g; 0.5 mol) was added followed by Et$_3$N (70 mL; 0.5 mol). The reaction mixture was stirred at 0° for 30 min and at 25° for 18 h and evaporated in vacuo. The residue dissolved in EtOAc (1.5 l) and was washed with 1M citric acid (2×500 mL) and sat. NaCl solution (500 mL), dried over MgSO$_4$, filtered and dicyclohexylamine (100 mL) added. After standing in the cold room for several hours, the white salt was collected and dried to yield 379.8 g (96.4%); mp 114°–118°.

The free acid was generated from the DCHA salt as follows: Z-Lys(Boc)-Lys(Boc)-OH.DCHA (200 g; 0.25 mol) was stirred in ether; 0.5N H$_2$SO$_4$ (800 mL each) until all the solid was dissolved. The ether phase was extracted, dried over MgSO$_4$, filtered and evaporated in vacuo to an oil which was used directly in the next step. $[\alpha]_D^{25}$ −3.06° (c 1, MeOH); $R_f$ 0.52 (CHCl$_3$:MeOH:AcOH; 80:5:1).

Anal. Calc. for $C_{30}H_{48}N_4O_9$ (608.75); C, 59.19; H, 7.95; N, 9.20. Found: C, 58.76; H, 7.95; N, 9.15.

(c)
N$^\epsilon$-t-Butyloxycarbonyl-L-lysyl-N$^\epsilon$-t-butyloxycarbonyl-L-lysine The oily product from the preceding step (0.25 mol) was dissolved in CH$_3$OH (1.2 l) and hydrogenated with 5% Pd-BaSO$_4$ (30 g) for 4 h in a Vibromixer apparatus. The reaction mixture was filtered through celite and evaporated to dryness to yield 102.5 g (86.4%) of white solid; mp 189°–190°; $[\alpha]_D^{25}$ +18.19° (c 1, CH$_3$OH); $R_f$ 0.73 (n-BuOH:AcOH:EtOAc:H$_2$O; 1:1:1:1).

Anal. Calc. for $C_{22}H_{42}N_4O_7$ (474.60): C, 55.68; H, 8.92; N, 11.81. Found: C, 55.59; N, 8.73; N, 11.83.

(d) N-Benzyloxycarbonyl-γ-t-butyl-L-glutamic acid N-hydroxysuccinimide ester

Z-Glu(OtBu)-OH (168.5 g; 0.5 mol) was dissolved in freshly distilled THF (1 l) and stirred at 0° in a 2-l, 3-neck round bottom flask fitted with a drying tube, mechanical stirrer and thermometer. While stirring at 0°, HOSu (63.6 g; 0.55 mol) and DCC (114 g; 0.55 mol) were added. The reaction mixture was stirred for 1 h at 0° and 18 h at 25°. At the end of this time the reaction mixture was filtered and the filtrate evaporated to dryness. The white solid was recrystallized from i-PrOH to yield 195.9 g (90.3%); mp 105°–106°; $R_f$ 0.66 (CHCl$_3$:CH$_3$OH:AcOH; 80:5:1); $[\alpha]_D^{25}$ −31.8° (c 1.8, EtOH).

(e)
N-Benzyloxycarbonyl-γ-t-butyl-L-glutamyl-N$^\epsilon$-t-butyloxycarbonyl-L-lysyl-N$^\epsilon$-t-butyloxycarbonyl-L-lysine (III)

A solution of Z-Glu(OtBu)-OSu (95.5 g; 0.22 mol; 1.1 eq.) in DMF (400 mL) was stirred at 0° in a 2-l; 3-neck round bottom flask fitted with a mechanical stirrer, thermometer and drying tube. H-Lys(Boc)-Lys(Boc)-OH (96.5 g; 0.2 mol) was added as a solid, portionwise, along with Et$_3$N (30.7 mL; 0.2 mol) and the pH of the reaction mixture adjusted to 8 with excess Et₃N [DMF (200 mL) was used to wash in all of the H-Lys(Boc)-Lys(Boc)-OH]. The reaction mixture was stirred at 0° for 1 h and at 25° for 18 h, then evaporated in vacuo. The residue was taken up in EtOAc (900 mL) and washed with 1M citric acid (2×400 mL) and sat. NaCl (600 mL), dried over MgSO₄, filtered and evaporated to ~½ volume. Ether (500 mL) was added and after cooling a white solid was collected to give 139.8 g (88%); mp 150°–152°; $R_f$ 0.83 (CHCl₃:CH₃OH:AcOH; 80:10:5); $R_f$ 0.49 (CHCl₃:CH₃OH:AcOH; 80:5:1); $[\alpha]_D^{25}$ −13.06 (c 1, CH₃OH).

Anal. Calc. for C₃₉H₆₃N₅O₁₂ (793.96): C, 59.00; H, 8.00; N, 8,82. Found: C, 58.77; H, 7.85; N, 8.93.

EXAMPLE 4

Synthesis of Fragment IV
(N-Benzyloxycarbonyl-β-t-butyl-L-aspartyl-L-leucyl-Nᵉ-t-butyloxycarbonyl-L-lysine)

(a) N-Benzyloxycarbonyl-L-leucine N-hydroxysuccinimide ester

Z-Leu-OH.DCHA (178.65 g; 0.4 mol) was stirred magnetically in ethyl acetate:0.5N H₂SO₄ (1 L:1 L) until all the white solid was in solution. The organic layer was collected, washed with 0.5N H₂SO₄ (3×300 mL) and distilled water (3×300 mL). The aqueous layers were combined and extracted with ethyl acetate. The organic layers were combined, dried (MgSO₄), filtered and evaporated. The resultant free acid (106.1 g; 0.4 mol) was dissolved in CH₂Cl₂ (300 mL) and placed in a 2 L, 3-necked round bottom flask fitted with a thermometer, drying tube and mechanical stirrer. N-Hydroxysuccinimide (50.63 g; 0.44 mol) and THF (100 mL) were added and the mixture stirred. The resultant solution was cooled (ice-bath), DCC (90.78 g; 0.44 mol) added and stirred at 0° for 1 h and 25° for 3.5 h. The reaction mixture was filtered and the filtrate evaporated in vacuo. The residue was dissolved in CH₂Cl₂ (450 mL), filtered (celite) hexane added to turbidity (1.1 L) and stored at 4° for 12 h. The crystals were filtered and dried yielding 122.8 g (84.7%) of product: m.p. 115°–117°; $[\alpha]_D^{25}$ −32.35° (c 1, dioxane).

(b)
N-Benzyloxycarbonyl-L-leucyl-Nᵉ-t-butyloxycarbonyl-L-lysine

A solution of Z-Leu-OSu (122.5 g, 0.338 mol) in DMF (1.2 L) was stirred at 0° in a 3 L, 3-necked round bottom flask fitted with a mechanical stirrer and thermometer. The H-Lys(Boc)-OH (83.26 g, 0.338 mol) was added and the solution stirred at 0° for 15 min. Triethylamine (47.6 mL, 0.338 mol) was added and the reaction mixture stirred at 0° for 30 min and 25° for 3 h. Additional triethylamine (20 mL) was added to maintain the pH at 8 and the reaction mixture stirred for an additional 20 h. At the end of this time, tlc showed some unreacted H-Lys(Boc)-OH and the reaction mixture was stirred for an additional 24 h (pH 8). The reaction mixture was cooled (0°), acidified with glacial acetic acid (160 mL) and evaporated in vacuo. The residue (oil) was dissolved in EtOAc (1.5 L) and washed with 1M citric acid (2×600 mL) and 10% NaCl (2×700 mL), dried (MgSO₄), filtered and concentrated in vacuo. The oily residue was dissolved in anhydrous ether (4 L) and dicyclohexylamine (70.7 mL) added followed by the addition of 1 L of ether. After standing in the cold room for 72 h, the white salt was collected and dried to yield 210.8 g (90%); m.p. 125°–128° (recrystallization of an analytical sample increased the m.p. to 143°–146°); $[\alpha]_D^{25}$ −4.17 (c 1, MeOH); $R_f$ 0.39 (CHCl₃:MeOH:AcOH; 85:10:5). The free acid was generated from the DCHA salt in the following manner: Z-Leu-Lys(Boc)-OH.DCHA (201.9 g, 0.291 mol) was stirred in EtOAC:0.5N H₂SO₄ (2 L:727 mL) until all the solid dissolved. The organic layer was separated, washed with 0.5N H₂SO₄ (730 mL), dried (MgSO₄) and evaporated in vacuo. Yield: 150.6 g (100%); $[\alpha]_D^{25}$ +3.38° (c 1, CHCl₃); $R_f$ 0.64 (CHCl₃:MeOH:AcOH; 85:10:5).

Anal. Calc. for C₂₅H₃₉N₃O₇ (493.6): C, 60.83; H, 7.96; N, 8.51. Found: C, 60.37; H, 8.08; N, 8.44.

(c) L-Leucyl-Nᵉ-tert-butyloxycarbonyl-L-lysine

A solution of Z-Leu-Lys(Boc)-OH 41.5 g, 0.084 mol) in methanol (210 mL) was hydrogenated in a Vibromixer apparatus using 10% Pd/C (5.0 g) for 3.5 h. The precipitated product dissolved on addition of H₂O (120 mL). The catalyst was removed by filtration (celite); washed twice with H₂O and the combined filtrate evaporated to near dryness. The residue was reevaporated from MeOH (2×) and Et₂O (2×). The solid product was collected, washed with Et₂O and dried to afford 26.9 g of white solid. Recrystallization from warm iPrOH (420 ml) and MeOH (350 mL) afforded, after drying, 24.6 g of white crystalline product (81.5%); mp 142°–143°; $R_f$ 0.63 (n-BuOH:AcOH:EtOAc:H₂O; 1-1-1-1); $[\alpha]_D^{25}$ +20.76° (c 1, MeOH). Anal: calcd. for C₁₇H₃₃N₃O₅ (359.47): C, 56.80; H, 9.25; N, 11.69. Found: C, 56.72; H, 9.55; N, 11.57.

(d) N-Benzyloxycarbonyl-β-tert-butyl-L-aspartic acid N-hydroxysuccinimide ester

Z-Asp(OtBu)-OH.DCHA (378 g; 0.750 mol) was stirred magnetically at 0° in a mixture of ethyl acetate:0.5N H₂SO₄ (3.0 L:1.875 L) until all the white solid was in solution. The organic layer was collected, washed with ice-cold 0.5N H₂SO₄ (1.8 L), water (3×1 L), dried (MgSO₄), filtered and evaporated in vacuo. Yield: 252 g (100%); $R_f$ 0.63 (CHCl₃:MeOH:AcOH; 85:10:5); $[\alpha]_D^{25}$ −10.10° (c 1, pyridine). The resultant free acid (252 g; 0.75 mol) and N-hydroxysuccinimide (94.95 g; 0.825 mol) were placed in a 12 L, 3-necked round bottom flask fitted with a thermometer, drying tube, mechanical stirrer and stirred at 25° in THF (4.2 L). After all the solids had dissolved, the reaction mixture was cooled (0°), DCC (170.2 g; 0.825 mol) and THF (0.75 L) added and stirred at 0° for 1 h and 25° for 5 h. The reaction mixture was filtered and the filtrate evaporated in vacuo. The residue was dissolved in CH₂Cl₂ (2 L) and stored (0°). The solution was filtered (to remove some more DCU) and the filtrate evaporated in vacuo. The residue was dissolved in CH₂Cl₂ (warm):hexane (1 L:4 L) and stored (0°). The resultant crystals were washed with hexane:CH₂Cl₂ (9:1) (1 L), hexane (1 L) and dried. Yield: 274 g (86.5%); m.p. 150°–151°; $[\alpha]_D^{25}$ −26.36° (c 1, DMF).

(e)
N-Benzyloxycarbonyl-β-tert-butyl-L-aspartyl-leucyl-Nᵉ-tert-butyloxycarbonyl-L-lysine, (IV)

A solution of Z-Asp(OtBu)-OSu (115.6 g; 0.275 mol) in DMF (1.16 L) was stirred at 0° in a 3 L, 3-necked round bottom flask fitted with a mechanical stirrer and thermometer. The H-Leu-Lys(Boc)-OH (89.86 g; 0.250 mol) was added followed by Et₃N (35.2 mL; 0.25 mol).

The reaction mixture was stirred at 0° for 0.5 h and at 25° for 1.5 h. Additional Et₃N (17 mL) was added (to maintain pH 8) and the reaction mixture stirred at 25° for 20 h. The reaction mixture was evaporated, dissolved in EtOAc (3 L), washed with 1M citric acid (3×1 L), H₂O (3×1 L), dried (MgSO₄) and evaporated in vacuo. The residual paste was dissolved in anhydrous ether (5 L) and stirred magnetically while DCHA (53.5 mL; 0.268 mol) was added slowly. After standing in the cold room (20 h) the white salt was collected and washed with anhydrous ether (2×0.5 L) and petroleum ether (2×0.5 L). Yield: 177 g (84%); m.p. 173°–174°; $[\alpha]_D^{25} -12.57°$ (c 1, MeOH).

Z-Asp(OtBu)-Leu-Lys(Boc)-OH.DCHA (198 g; 0.234 mol) was stirred at 0° in a mixture of EtOAc:0.5N H₂SO₄ (3.2 L:1.19 L) until all the solid was dissolved. The organic layer was collected, washed with H₂O (4×1 L), dried (MgSO₄), filtered and evaporated in vacuo. The residue (froth) was triturated with pet. ether and dried. Yield: 165.5 g (100%); $[\alpha]_D^{25} -1.16°$ (c 1, CHCl₃); $R_f$ 0.73 (CHCl₃:MeOH:AcOH; 85:10:5).

Anal. Calc. for C₃₃H₅₂N₄O₁₀ (664.8): C, 59.62; H, 7.88; N, 8.43. Found: C, 59.38; H, 8.13; N, 8.45.

EXAMPLE 5

Synthesis of Fragment V
(Z-Thr(tBu)-Ser(tBu)-Ser(tBu)-Glu(OtBu)-Ile-Thr(tBu)-Thr(tBu)-Lys(Boc)-OH)

(a)
N-Benzyloxycarbonyl-O-t-butyl-L-threonyl-N$^\epsilon$-t-butyloxycarbonyl-L-lysine phenyl ester Z-Thr(tBu)-OH (180.35 g, 583 mmol) was dissolved in 850 ml DMF and cooled to −35° C. While stirring at −35° C., N-methylmorpholine (64.2 ml, 583 mmol) was added, followed by the addition of isobutyl chloroformate (76.2 ml, 583 mmol). The reaction mixture was activated for 2 min. at −15° C. and quickly cooled to −30° C. A precooled solution (−25° C.) of H-Lys(Boc)-OPh.Tos-OH (262.1 g, 530 mmol) in 800 ml DMF and N-methylmorpholine (58.4 ml, 530 mmol) were added simultaneously. The reaction mixture was stirred for 15 min. at −15° C. and 1 h at 25° C. and evaporated in vacuo. The residue was dissolved in 3 l ethyl acetate and washed with 10% Na₂CO₃ sol. (3×1.5 l), satd. NaCl sol. (4×1 l), 5% KHSO₄/10% K₂SO₄ sol. (3×1.5 l), and satd. NaCl-sol., dried over Na₂SO₄, filtered and evaporated in vacuo. The residue was crystallized from ether (1 l)/hexane (3 l) or from isopropyl acetate (1.5 l)/hexane (4 l).

Yield: 258.4 g (79.5%); mp. 72° C.(*); $[\alpha]_D^{20} +11.8°$ (c=1, CHCl₃).

Anal. Calc. for C₃₃H₄₇N₃O₈ (613.75): C, 64.58; H, 7.72; N, 6.85. Found: C, 64.42; H, 7.90; N, 6.57.

(*)When the material was crystallized from isopropyl acetate/hexane a melting point of 106° C. resulted.

(b)
N-Benzyloxycarbonyl-O-t-butyl-L-threonyl-O-t-butyl-L-threonyl-N-ε-t-butyloxycarbonyl-L-lysine phenyl ester Z-Thr(tBu)-Lys(Boc)-OPh (251.6 g, 410 mmol) dissolved in 1 l DMF was hydrogenated in the presence of Tos-OH.H₂O (78 g, 410 mmol) and 10% Pd-C. After the hydrogenation was completed the catalyst was filtered off.
Z-Thr(tBu)-OH (139.2 g, 450 mmol) was dissolved in 700 ml DMF and cooled to −35° C. While stirring at −35° C., N-methylmorpholine (49.6 ml, 450 mmol) was added, followed by the addition of isobutyl chloroformate (58.8 ml, 450 mmol). The reaction mixture was activated for 2 min. at −15° C. and quickly cooled to −30° C. The precooled (−25° C.) DMF solution from the hydrogenation step and N-methylmorpholine (45.2 ml, 410 mmol) were added simultaneously. The reaction mixture was stirred for 15 min. at −15° C. and 1 h at 25° C. and evaporated in vacuo. The residue was dissolved in 2 l ethyl acetate and washed with 10% Na₂CO₃ sol. (3×1.5 l), satd. NaCl-sol. (1×1 l), 5% KHSO₄/10% K₂SO₄ sol. (3×1.5 l), and satd. NaCl-sol., dried over Na₂SO₄, filtered and evaporated in vacuo. The residue was crystallized from ether (1 l)/hexane (4 l).

Yield: 240.2 g, (76%); mp. 124° C.; $[\alpha]_D^{20} +26.4°$ (c=1, CHCl₃)

Anal. Calc for C₄₁H₆₂N₄O₁₀ (770.97): C, 63.87; H, 8.11; N, 7.27. Found: C, 63.81; H, 8.56; N, 7.06.

(c)
N-Benzyloxycarbonyl-L-isoleucyl-O-t-butyl-L-threonyl-O-t-butyl-L-threonyl-N$^\epsilon$-t-butyloxycarbonyl-L-lysine phenyl ester A solution of Z-Thr(tBu)-Thr(tBu)-Lys(Boc)-OPh (346.9 g, 450 mmol) in 1 l DMF was hydrogenated in the presence of Tos-OH.H₂O (85.6 g, 450 mmol) and 10% Pd-C. After the hydrogenation was completed the catalyst was filtered off. Z-Ile-OH (132.66, 500 mmol) was dissolved in 700 ml DMF and cooled to −35° C. While stirring at −35° C., N-methylmorpholine (55 ml, 500 mmol) was added, followed by the addition of iso-butyl chloroformate (65 ml, 500 mmol). The reaction mixture was activated for 5 min. at −15° C. and quickly cooled to −20° C. The precooled DMF solution (−25° C.) from the hydrogenation step and N-methylmorpholine (50 ml, 450 mmol) were added simultaneously. The reaction mixture was stirred for 15 min. at −15° C. and 1 h at 25° C. and evaporated in vacuo. The residue was dissolved in 3 l ethyl acetate and washed with 10% Na₂CO₃ sol. (2×1.5 l), satd. NaCl-sol. (1×1 l), 5% KHSO₄/10% K₂SO₄ sol. (2×1.5 l) and satd. NaCl-sol., dried over Na₂SO₄, filtered and evaporated in vacuo. The residue was crystallized from ethyl acetate (2 l)/ether (2 l).

Yield: 296 g, (74.5%); mp. 150° C.; $[\alpha]_D^{20} +24.2°$ (c=1, CHCl₃) C₄₇H₇₃N₅O₁₁ (884.12).

Anal. Calc. for C₄₇H₇₃N₅O₁₁ (884.12): C, 63.85; H, 8.32; N, 7.92. Found: C, 63.77; H, 8.34; N, 7.92.

(d)
N-Benzyloxycarbonyl-O-t-butyl-L-seryl-γ-t-butyl-L-glutamic acid phenyl ester A solution of Z-Glu(OtBu)-OPh (198.4 g, 480 mmol) in 1 l DMF was hydrogenated in the presence of Tos-OH.H₂O (91.3 g, 480 mmol) and 10% Pd-C (20 g). After the hydrogenation was completed the catalyst was filtered off. Z-Ser(tBu)—OH (147.7 g, 500 mmol) was dissolved in 1.5 l DMF and cooled to −25° C. N-Methylmorpholine (55.1 ml, 500 mmol) and isobutyl chloroformate (65.35 ml, 500 mmol) were added and 2 min. were allowed for activation at −15° C. The precooled DMF solution (−25° C.) from the hydrogenation step and N-methylmorpholine (52.9 ml, 480 mmol) were added simultaneously. The reaction mixture was stirred for 15 min. at −15° C. and 1 h at 25° C. and evaporated in vacuo. The residue was dissolved in 4 l ethyl acetate extracted with 10% NaHCO₃-sol., 5% KHSO₄/10%K₂SO₄-sol. and satd. NaCl-sol., dried over Na$_2$SO$_4$, filtered and evaporated. The residue was crystallized from ether/hexane.

Yield: 223 g (83.5%) mp. 97° C.; $[\alpha]_D^{20}+16.2°$ (c=1, CHCl$_3$).

Anal. Calc. for C$_{30}$H$_{40}$N$_2$O$_8$ (556.66): C, 64.73; H, 7.24; N, 5.03. Found: C, 64.82; H, 7.22; N, 5.10.

(e)
N-Benzyloxycarbonyl-O-t-butyl-L-seryl-O-t-butyl-L-seryl-γ-t-butyl-L-glutamic acid phenyl ester A solution of Z-Ser(tBu)-Glu(OtBu)-OPh (256.1 g, 460 mmol) in 1.2 l DMF was hydrogenated in the presence of Tos-OH.H$_2$O (87.5 g, 460 mmol) and 10% Pd-C (~25 g). After the hydrogenation was completed the catalyst was filtered off. Z-Ser(tBu)-OH (145.6 g, 493 mmol) was dissolved in 1.4 l DMF and cooled to −25° C. N-Methylmorpholine (54.3 ml, 493 mmol) and isobutyl chloroformate (64.4 ml, 493 mmol) were added to this solution and 2 min. were allowed for activation at −15° C. The precooled DMF solution from the hydrogenation step and N-methylmorpholine (50.7 ml, 460 mmol) were added simultaneously. The reaction mixture was stirred for 15 min. at −15° C. and 1 h at 25° C. and evaporated in vacuo. The residue was dissolved in 4 l ethyl acetate and extracted with 10% NaHCO$_3$-sol., 5% KHSO$_4$/10% K$_2$SO$_4$-sol., and satd. NaCl-sol., dried over Na$_2$SO$_4$, filtered and evaporated. The residue was crystallized from ethyl acetate/hexane.

Yield: 262 g, (81.4%); mp. 130°-31° C.; $[\alpha]_D^{20}+21.6°$ (c=1, CHCl$_3$).

Anal. Calc. for C$_{37}$H$_{53}$N$_3$O$_{10}$ (699.84): C, 63.50; H, 7.63; N, 6.00. Found: C, 63.37; H, 7.95; N, 6.03. From the motherliquor another crop of 26 g (8%) was obtained. Total yield: 288 g (89.5%).

(f)
N-Benzyloxycarbonyl-O-t-butyl-L-threonyl-O-t-butyl-L-seryl-O-t-butyl-L-seryl-α-t-butyl-L-glutamic acid phenyl ester A solution of Z-Ser(tBu)-Ser(tBu)-Glu(OtBu)-OPh (270 g, 386 mmol) in 1.2 l DMF was hydrogenated in the presence of Tos-OH.H$_2$O (73.4 g, 386 mmol) and 10% Pd-C (30 g). After the hydrogenation was completed the catalyst was filtered off. Z-Thr(tBu)-OH (119.4 g, 386 mmol) was dissolved in 1.2 l DMF and cooled to −25° C. N-Methylmorpholine (42.5 ml, 386 mmol) and isobutyl chloroformate (50.5 ml, 386 mmol) were added to this solution and 2 min. were allowed for activation at −15° C. The precooled DMF solution from the hydrogenation step and N-methylmorpholine (42.5 ml, 386 mmol) were added simultaneously. The reaction mixture was stirred for 15 min. at −15° C. and 1 h at 25° C. and evaporated in vacuo. The residue was dissolved in 4 l ethyl acetate, extracted with 10% NaHCO$_3$-sol., 5% KHSO$_4$/10% K$_2$SO$_4$-sol., and satd. NaCl-sol., dried over Na$_2$SO$_4$, filtered and evaporated. The residue was crystallized from ethyl acetate/hexane.

Yield: 270.5 g (81.8%); mp. 144°-45° C.; $[\alpha]_D^{20}+37.2°$ (c=1, CHCl$_3$).

Anal. Calc. for C$_{45}$H$_{68}$N$_4$O$_{12}$ (857.06): C, 63.05; H, 8.00; N, 6.54. Found: C, 62.71; H, 8.18; N, 6.57.

From the motherliquor another crop of 19.6 g (6%) was obtained. Total yield: 290.1 g (87.7%).

(g) Z-Thr(tBu)-Ser(tBu)-Ser(tBu)-Glu(OtBu)-OH

Z-Thr(tBu)-Ser(tBu)-Ser(tBu)-Glu(OtBu)-OPh (128.5 g, 150 mmol) was dissolved in 835 ml acetone/135 ml water, and 30% H$_2$O$_2$ (15.3 ml, 150 mmol) was added under stirring at 25° C. The reaction mixture was adjusted to, and maintained at, pH 10.5 for 3 h by the addition of 2N NaOH using an autotitrator. The reaction solution was diluted with 400 ml water and acidified to pH 3 with 1N HCl. The organic solvent was evaporated off and the crystalline solid filtered off. It was recrystallized from acetone/water and from ethylacetate/hexane.

Yield: 105 g (89.6%); m.p. 79°-83° C.; $[\alpha]_D^{20}+17.4°$ (c=0.5, MeOH).

Anal.: Calc. for C$_{39}$H$_{64}$N$_4$O$_{12}$ (780.96): C 59.98, H 8.26, N 7.17; Found: C 59.71, H 8.29, N 7.15.

(h)
Z-Thr(tBu)-Ser(tBu)-Ser(tBu)-Glu(OtBu)-Ile-Thr(tBu)-Thr(tBu)-Lys(Boc)-OPh

A solution of Z-Ile-Thr(tBu)-Thr(tBu)-Lys(Boc)-OPh (58.35 g, 66 mmol) in 1 l DMF was hydrogenated in the presence of Tos-OH.H$_2$O (12.55 g, 66 mmol) and 10% Pd-C. After the hydrogenation was completed the catalyst was filtered off.

Z-Thr(tBu)-Ser(tBu)-Ser(tBu)-Glu(OtBu)-OH (51.5 g, 66 mmol) was dissolved in 1.5 l DMF and cooled to −18° C. While stirring at −18° C., N-methylmorpholine (7.27 ml, 66 mmol) and isobutyl chloroformate (8.62 ml, 66 mmol) were added to the solution. The reaction mixture was activated for 2 min. at −15° C. before the precooled DMF solution (−20° C.) from the hydrogenation step and N-methylmorpholine (7.27 ml, 66 mmol) were added simultaneously. The reaction mixture was stirred for 15 min. at −15° C. and 1 h at 25° C. and poured into H$_2$O (10 l), which contained NaHCO$_3$ (50 g). The product was collected by filtration, washed with H$_2$O and redissolved in CHCl$_3$ (3 l). The CHCl$_3$ phase was extracted with H$_2$O and satd. NaCl sol., dried over Na$_2$SO$_4$ and concentrated. The product precipitated by the addition of hexane.

Yield: 90.2 g (90%) m.p. 226°-228° C.; $[\alpha]_D^{20}+19°$ (c=1, CHCl$_3$).

Anal.: Calc. for C$_{78}$H$_{129}$N$_9$O$_{20}$ (1512.93): C 61.92, H 8.59, N 8.33; Found: C 61.94, H 8.55, N 8.34.

(i)
Z-Thr(tBu)-Ser(tBu)-Ser(tBu)-Glu(OtBu)-Ile-Thr(tBu)-Thr(tBu)-Lys(Boc)-OH (v)

A solution of Z-Thr(tBu)-Ser(tBu)-Ser(tBu)-Glu(OtBu)-Ile-Thr(tBu)-Thr(tBu)-Lys(Boc)-OPh (48.4 g, 32 mmol) in 250 ml TFE/25 ml H$_2$O was treated with 30% H$_2$O$_2$ (4.1 ml, 40 mmol). The reaction mixture was adjusted to pH 10.5 by the addition of 4N NaOH and maintained at this pH over a period of 2 h. The reaction solution was acidified to pH 3 with 1N H$_2$SO$_4$ and poured into 2 l H$_2$O. The precipitate was filtered off, washed with H$_2$O and triturated with ethanol and ether.

Yield: 39.7 g (86%) m.p. 212°-214° C.; $[\alpha]_D^{20}+26.6°$ (c=1, CHCl$_3$).

Anal.: Calc. for C$_{72}$H$_{125}$N$_9$O$_{20}$ (1436.84): C 60.19, H 8.77, N 8.77; Found: C 59.77, H 8.86, N 8.68.

EXAMPLE 6

Synthesis of Fragment
VI(Ac-Ser(tBu)-Asp(OtBu)-Ala-Ala-Val-Asp(OtBu)-OH)

(a) Z-Asp(OtBu)-OPh

Z-Asp(OtBu)-OH (32.3 g, 100 mmol) was dissolved in 250 ml ethyl acetate and cooled to 0° C. To this stirred solution pyridine (12 ml, 150 mmol), phenol (11.3 g, 120 mmol) and a precooled solution of DCC (22.7 g, 110 mmol) in 50 ml ethyl acetate were added. Stirring was continued for 2 h at 0° C. Acetic acid (2 ml) was added and the reaction mixture was stirred for another 10 min. Dicyclohexylurea was filtered off and the filtrate was washed with 10% NaHCO₃ sol., satd. NaCl sol., 5% KHSO₄/10% K₂SO₄ sol. and satd. NaCl sol., dried over Na₂SO₄, filtered and evaporated in vacuo. The residue was crystallized (twice) from ether/hexane.

Yield: 26.3 g (66%); m.p. 64°–65° C.; $[\alpha]_D^{20}$ −32.7° (c=1, DMF).

Anal.: Calc. for $C_{22}H_{25}NO_6$ (399.44): C 66.15, H 6.31, N 3.51; Found: C 66.09, H 6.30, N 3.52.

(b) Z-Val-Asp(OtBu)-OPh

A solution of Z-Asp(OtBu)-OPh (99.9 g, 250 mmol) in 500 ml DMF was hydrogenated in the presence of Tos-OH.H₂O (47.55 g, 250 mmol) and 10% Pd-C (20 g). After the hydrogenation was completed the catalyst was filtered off.

Z-Val-OH (62.8 g, 250 mmol) was dissolved in 500 ml DMF and cooled to −25° C. N-Methylmorpholine (27.5 ml, 250 mmol) and isobutyl chloroformate (32.7 ml, 250 mmoL) were added and 2 min. were allowed for activation at −20° C. The precooled DMF solution from the hydrogenation step and N-methylmorpholine (27.5 ml, 250 mmol) were added simultaneously. The reaction mixture was stirred for 15 min. at −15° C. and 1 h at 25° C. and poured into 4 l 0.25M NaHCO₃ sol.. The precipitate was filtered off, washed with water and dried. The product was crystallized from ethyl acetate/hexane.

Yield: 102 g (82%) m.p. 139°–141° C.; $[\alpha]_D^{20}$ +8.4° (c=1, CHCl₃).

Anal.: Calc. for $C_{27}H_{34}N_2O_7$ (498.58): C, 65.04, H 6.87, N 5.62; Found: C 65.02, H 6.99, N 5.57.

(c) Z-Ala-Val-Asp-(OtBu)-OPh

A solution of Z-Val-Asp(OBu)-OPh (99.7 g, 200 mmol) in 500 ml DMF was hydrogenated in the presence of Tos-OH.H₂O (38 g, 200 mmol) and 10% Pd-C (20 g). After the hydrogenation was completed the catalyst was filtered off.

Z-Ala-OH (44.6 g, 200 mmol) was dissolved in 500 ml DMF and cooled to −25° C. N-Methylmorpholine (22.1 ml, 200 mmol) and isobutyl chloroformate (26.1 ml, 200 mmol) were added and 2 min. were allowed for activation at −20° C. The precooled DMF solution from the hydrogenation step and N-methylmorpholine (22.1 ml, 200 mmol) were added simultaneously. The reaction mixture was stirred for 15 min. at −15° C. and 30 min. at 25° C. and poured into 3 l 0.25M NaHCO₃ sol.. The precipitate was filtered off, washed with water and dried. The product was crystallized from ethyl acetate.

Yield: 102.5 g (90%); m.p. 156°–157° C.; $[\alpha]_D^{20}$ −14.5° (c=1, CHCl₃).

Anal.: Calc. for $C_{30}H_{39}N_3O_8$ (569.66): C 63.25, H 6.90, N 7.38; Found: C 63.13, H 6.89, N 7.34.

(d) N-Benzyloxycarbonyl-β-t-butyl-L-aspartyl-L-alanine benzyl ester

Z-Asp(OtBu)-OH (161.6 g, 500 mmol) was dissolved in 750 ml DMF and cooled to −30° C. To the stirred solution N-methylmorpholine (55.1 ml, 500 mmol) and isobutyl chloroformate (65.4 ml. 500 mmol) were added and 2 min allowed for activation at −15° C. A precooled DMF (500 ml) solution of H-Ala-OBzl.Tos-OH (193.3 g, 550 mmol) and N-methylmorpholine (60.6 ml. 550 mmol) were added simultaneously. The reaction mixture was stirred at −15° C. for 15 min and at 25° C. for 1 h. The reaction mixture was evaporated in vacuo and the residue was taken up in 3.5 l ethyl acetate. The organic layer was extracted with 10% Na₂CO₃-sol., water, 5% KHSO₄/10% K₂SO₄-sol. and saturated NaCl sol., dried over Na₂SO₄, filtered and evaporated in vacuo. Crystallisation was achieved at 0° C. from ethyl acetate (0.5 l)/hexane (5 l).

Yield: 202.9 g (83.8%); mp. 51° C.; $[\alpha]_D^{25}$ −26.9° (c=1, MeOH).

Anal.: Calc. for $C_{26}H_{32}N_2O_7$ (484.54): C, 64.45; H, 6.66; N, 5.78. Found: C, 64.45; H, 6.69; N, 5.75.

(e) N-Benzyloxycarbonyl-O-t-butyl-L-seryl-β-t-butyl-L-aspartyl-L-alanine

A solution of Z-Ser(tBu)-OH (29.5 g, 100 mmol) in 300 ml ethyl acetate was cooled to 0°. N-Hydroxysuccinimide (11.5 g, 100 mmol) and DCC (22.7 g. 110 mmol) were added and the reaction stirred at 0° for 1 h and at 25° for 20 h. The unreacted DCC was destroyed by adding Tos-OH.H₂O (0.2 g) and water (5 ml). After 1 h stirring at 25° the urea was filtered off and the filtrate evaporated in vacuo.

Z-Asp(OtBu)-Ala-OBzl (43.6 g, 90 mmol) was dissolved in 1 liter DMF and hydrogenated in the presence of Tos-OH.H₂O (17.1 g, 90 mmol) and 10% Pd-C. After the hydrogenation was completed the catalyst was filtered off. The filtrate was cooled to 0°, neutralized with N-methylmorpholine (9.9 ml, 90 mmol) and added to Z-Ser(tBu)-OSu. Another portion of N-methylmorpholine (9.9 ml, 90 mmol) was added and the reaction mixture was stirred at 0° for 1 h and at 25° for 18 h. 2-Diethylamino-ethylamine (2.83 ml, 20 mmol) was added to the reaction mixture and stirring was continued for 4 h. The solution was evaporated in vacuo, the residue dissolved in 0.5N NaOH (0.5 l) and extracted with ether (3×0.2 l). To the alkaline phase 0.4 l ethyl acetate was added and acidified with 5% KHSO₄/10% K₂SO₄-solution. The acidic layer was again extracted with ethyl acetate (2×0.3 l). The combined organic layers were washed with 5% KHSO₄/10% K₂SO₄-sol. (1×0.3 l) and saturated NaCl-sol., dried over Na₂SO₄, filtered and evaporated in vacuo.

Yield: 37 g (76.5%)Oil.

(f) N-Acetyl-O-t-butyl-L-seryl-β-t-butyl-L-aspartyl-L-alanine

The oily product Z-Ser(tBu)-Asp(OtBu)-Ala-OH (16.3 g, 30 mmol) from the preceding step was dissolved in 200 ml methanol and hydrogenated with 10% Pd-C. The catalyst was filtered off and the filtrate evaporated to dryness. The residue was dissolved in 100 ml DMF, cooled to 0° and N-methylmorpholine (6.6 ml. 60 mmol) and acetic anhydride (4.25 ml, 45 mmol) were added under stirring. The reaction mixture was stirred for 15 min at 25° and evaporated in vacuo. The residue was dissolved in 1N NaOH and extracted with ethyl acetate. The alkaline phase was acidified with 5% KHSO₄/10% K₂SO₄-sol., saturated with K₂SO₄ and several times extracted with ethyl acetate. The combined organic layers were washed with saturated NaCl-sol., dried over Na₂SO₄ and evaporated to dryness. The residue was crystallized from isopropyl acetate/ether.

Yield: 8.4 g (62.7%); m.p. 112°; $[\alpha]_D^{25} -16.6°$ (c=5, MeOH).

Anal. Calc. for $C_{20}H_{35}N_3O_8$ (445.51): C, 53.92; H, 7.92; N, 9.43. Found: C, 54.03; H, 8:00; N, 9.34.

(g)

Ac-Ser(tBu)-Asp(OtBu)-Ala-Ala-Val-Asp(OtBu)-OPh

A solution of Z-Ala-Val-Asp(OtBu)-OPh (22.8 g, 40 mmol) in 250 ml DMF was hydrogenated in the presence of Tos-OH.H₂O (7.6 g, 40 mmol) and 10% Pd-C. After the hydrogenation was completed the catalyst was filtered off.

Ac-Ser(tBu)-Asp(OtBu)-Ala-OH (17.8 g, 40 mmol) was dissolved in 400 ml DMF and cooled to −20° C. While stirring at −20° C., N-methylmorpholine (4.4 ml, 40 mmol) was added, followed by the addition of isobutyl chloroformate (5.22 ml, 40 mmol). The reaction mixture was activated for 2 min. at ∼ −18° C. The precooled DMF solution (−20° C.) from the hydrogenation step and N-methylmorpholine (4.4 ml, 40 mmol) were added simultaneously. The reaction mixture was stirred for 15 min. at −15° C. and 30 min. at 25° C. and poured into 2 l water, containing NaHCO₃ (30 g). The precipitate was collected by filtration, washed with water and dried.

Yield: 30.5 g (88.3%); m.p. 233°-235° C.; $[\alpha]_D^{20} -53.8°$ (c=1, TFE).

Anal.: Calc. for $C_{42}H_{66}N_6O_{13}$ (863.02): C 58.45, H 7.71, N 9.74; Found: C 58.29, H 7.75, N 9.89.

(h)

Ac-Ser(tBu)-Asp(OtBu)-Ala-Ala-Val-Asp(OtBu)-OH (VI)

Ac-Ser(tBu)-Asp(OtBu)-Ala-Ala-Val-Asp(OtBu)-OPh (30.2 g, 35 mmol) was dissolved in 180 ml TFE and 20 ml water and 30% H₂O₂ (3.9 ml, 38 mmol) was added. The reaction mixture was adjusted to pH 10.5 with 4N NaOH and stirred for 2 h at 25° C. The resulting dark brown solution was poured into 2.1 l 0.05N H₂SO₄ and the resulting precipitate was filtered off, washed with water and crystallized from ethanol.

Yield: 21.5 g (78%); m.p. 223°-224° C.; $[\alpha]_D^{20} -46.1°$ (c=1, TFE).

Anal.: Calc. for $C_{36}H_{62}N_6O_{13}$ (786.92): C 54.95, H 7.94, N 10.68; Found: C 54.78, H 8.07, N 11.04.

EXAMPLE 7

Synthesis of Thymosinα₁

(a)

Z-Glu(OtBu)-Val-Val-Glu(OtBu)-Glu(OtBu)-Ala-Glu(OtBu)-Asn-OtBu

A solution of Z-Glu(OtBu)-Val-Val-Glu(OtBu)-OH (II, 35.5 g, 0.049 mol) and H-Glu(OtBu)-Ala-Glu(OtBu)-Asn-OtBu (I, 31.5 g, 0.05 mol) in DMF (850 mL) was cooled to 0° and HOBt (22.7 g, 0.148 mol, 3 eq.) was added with mechanical stirring. DCC (15.3 g, 0.074 mol, 1.65 eq.) was added and the pH was adjusted to 7.5-8.0 by addition of N-methylmorpholine (∼15 mL). Stirring proceeded for 1 hr at 0° and 23 hr at 25°, filtered and the filtrate poured into H₂O (8 L) and stirred for 1.5 h. The product was collected by filtration, washed with H₂O (8 L), dried and washed with MeOH (4×250 mL) and dried in vacuo to give 46.8 g. Recrystallization from MeOH gave a white solid. Yield: 39.6 g (60%); mp 244°-245°, $[\alpha]_D^{25} -20.65°$ (c 0.5, DMSO); $R_f$ 0.35 (CHCl₃:MeOH:AcOH; 80-5-1).

Anal. calc. for $C_{65}H_{105}N_9O_{20}$ (1332.6): C, 58.59; H, 7.94; N, 9.45. Found: C, 58.42; H, 7.85; N, 9.72.

(b)

H-Glu(OtBu)-Val-Val-Glu(OtBu)-Glu(OtBu)-Ala-Glu(OtBu)-Asn-OtBu

A solution of Z-Glu(OtBu)-Val-Val-Glu(OtBu)-Glu(OtBu)-Ala-Glu(OtBu)-Asn-OtBu 42.6 g; 32.0 mmol) in DMF (650 mL) containing 10% Pd-BaSO₄ (15.0 g) was hydrogenated in a Vibromixer apparatus for 3 h. The reaction mixture was filtered through a bed of celite which was washed with DMF (5×250 mL). The combined filtrate was evaporated to 600 mL and DMSO (300 mL) added. The resultant solution was used fo the next stage of synthesis. A portion was evaporated to dryness, taken up in MeOH and precipitated with Et₂O. The resultant gel was filtered, washed with Et₂O and dried in vacuo; mp 246°-249° dec; $[\alpha]_D^{25} -18.78°$ (c 1, DMF); $R_f$ 0.78 (n-BuOH:AcOH:Pyr:H₂O; 1-1-1-1). Anal. calc. for $C_{57}H_{99}N_9O_{18}$ (1198.46): C, 57.13; H, 8.33; N, 10.52. Found: C, 56.83; H, 8.32; N, 10.39.

(c)

Z-Glu(OtBu)-Lys(Boc)-Lys(Boc)-Glu(OtBu)-Val-Val-Glu(OtBu)-Glu(OtBu)-Ala-Glu(OtBu)-Asn-OtBu

The DMF:DMSO-containing solution of H-Glu(OtBu)-Val-Val-Glu(OtBu)-Glu(OtBu)-Ala-Glu(OtBu)-Asn-OtBu (∼32 mmol) from (b) was combined with Z-Glu(OtBu)-Lys(Boc)-Lys(Boc)-OH (III, 36.8 g, 46 mmol, 1.44 eq.) and HOBt (14.7 g, 96 mmol, 3 eq.) added and the solution cooled to 0°. DCC (10.9 g, 52 mmol, 1.65 eq.) was added to the cold stirring (mechanical) reaction mixture and the pH was maintained at 7.5-8.0 by addition of N-methylmorpholine (21 mL). Stirring proceeded for 2 h at 0° and 21 h at 25°. The resultant gelatenous reaction mixture was poured into H₂O (9.0 L) and stirred for 4 h. The product was collected by filtration, washed with H₂O (8×500 mL), dried and washed with MeOH using the centrifuge to separate the 2 phases. When all the dicyclohexylurea was removed the product was combined and dried in vacuo to give 45.22 g (71.5%); mp 312° dec; $[\alpha]_D^{25} -18.20°$ (c 1, DMSO); $[\alpha]_D^{25} -13.27°$ (c 1, TFE); $R_f$ 0.81 (n-BuOH:AcOH:Pyr:H₂O; 15-3-10-12); $R_f$ 0.52 (CHCl₃:MeOH:AcOH; 85-10-5).

Anal. calc. for $C_{96}H_{160}N_{14}O_{29}$ (1974.4): C, 58.40; H, 8.17; N, 9.93. Found: C, 57.84; H, 8.28; N, 9.94.

(d)

H-Glu(OtBu)-Lys(Boc)-Lys(Boc)-Glu(OtBu)-Val-Val-Glu(OtBu)-Glu(OtBu)-Ala-Glu(OtBu)-Asn-OtBu

A solution of Z-Glu(OtBu)-Lys(Boc)-Lys(Boc)-Glu(OtBu)-Val-Val-Glu(OtBu)-Glu(OtBu)-Ala-Glu(OtBu)-Asn-OtBu (45.0 g, 23 mmol) in TFE (1.1 L) containing 10% Pd-BaSO₄ (15 g) was hydrogenated in a Vibromixer apparatus for 3 h. The reaction mixture was filtered through celite which was washed with TFE (3×100 mL). The combined filtrate was evaporated to dryness and taken up in DMF:DMSO (1300 mL:650 mL) for use in the next stage of synthesis. A portion of the residue was precipitated from TFE-H₂O, filtered and dried in vacuo; mp 326°-327°; $[\alpha]_D^{25} -17.65°$ (c 1, DMSO); $R_f$ 0.73 (n-BuOH:AcOH:EtOAc:H₂O; 1-1-1-1). Anal. calc. for $C_{88}H_{154}N_{14}O_{27}.H_2O$ (1876.27): C, 56.33; H, 8.49; N, 10.45. Found: C, 56.40; H, 8.69; N, 10.55.

(e)
Z-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn-OtBu

The DMF:DMSO-containing solution of H-Glu(OtBu)-Lys(Boc)-Lys(Boc)-Glu(OtBu)-Val-Val-Glu(OtBu)-Glu(OtBu)-Ala-Glu(OtBu)-Asn-OtBu (~23 mmol) from step (d) was combined with Z-Asp(OtBu)-Leu-Lys(Boc)-OH (IV, 18.6 g, 28.0 mmol, 1.2 eq.) and HOBt (10.62 g, 69.0 mmol, 3.0 eq.) added and the solution cooled to 0°. DCC (7.87 g, 38.0 mmol, 1.65 eq.) was added to the cold stirring (mechanical) reaction mixture and the pH was maintained at 7.5-8.0 by addition of N-methylmorpholine (~17 mL). Stirring proceeded for 1 h at 0° and 23 h at 25°. The resultant reaction mixture was poured into $H_2O$ (10 L) and stirred for 1.5 h. The product was collected by filtration, washed with $H_2O$ (5 L), dried and washed with MeOH using the centrifuge to separate the 2 layers. When all the dicyclohexylurea was removed the product was pooled and dried in vacuo to give 44.56 g (77.9%); mp >330°; $[\alpha]_D^{25} -11.56°$ (c 1, TFE); $R_f$ 0.16 ($CHCl_3$:MeOH:AcOH; 80-5-1); $R_f$ 0.36 ($CHCl_3$:MeOH:TFE:AcOH; 85-10-2.5-1).

Anal. calc. for $C_{121}H_{204}N_{18}O_{36}$ (2487.05): C, 58.43; H, 8.27; N, 10.13. Found: C, 57.96; H, 8.08; N, 10.16.

(f)
H-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn-OtBu

A solution of Z-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn-OtBu (35.36 g, 14.22 mmol) in TFE (720 mL) containing 5% Pd-$BaSO_4$ (11.8 g) was hydrogenated in a Vibromixer apparatus for 4 h. The reaction mixture was filtered through celite and evaporated to near dryness and precipitated with $H_2O$ (2 L). The product was collected by filtration and dried in vacuo.

Yield: 32.74 g (95.1%); mp >320° $[\alpha]_D^{25} -6.54°$ (c 1, TFE); $R_f$ 0.42 ($CHCl_3$: MeOH:AcOH; 85-10-5). Anal. calc. for $C_{113}H_{198}N_{18}O_{34}\cdot3H_2O$ (2406.9): C, 56.39; H, 8.54; N, 10.48 Found: C, 56.32; H, 8.28; N, 10.55.

(g)
Z-Thr(tBu)-Ser(tBu)-Ser(tBu)-Glu(OtBu)-Ile-Thr(tBu)-Thr(tBu)-Lys(Boc)-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn-OtBu

Z-Thr(tBu)-Ser(tBu)-Ser(tBu)-Glu(OtBu)-Ile-Thr(tBu)-Thr(tBu)-Lys(Boc)-OH (V, 5.74 g, 4 mmol) and HOBt (1.08 g, 8 mmol) were added to a solution of H-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn-OtBu$\cdot3H_2O$ (4.8 g, 2 mmol) in 150 ml $CHCl_3$. The mixture was stirred for about 1 h at 25° C. and cooled to 5° C. before DCC (1.03 g, 5 mmol) dissolved in 50 ml $CHCl_3$ was added. Stirring proceeded for 30 min. at 5° C. and 70 h at 25° C. The gelatinous reaction mixture was poured into hexane. The resulting precipitate was filtered off, washed with 5% $NaHCO_3$ sol. and $H_2O$ and triturated with hot ethanol and methanol and dried in vacuo.

Yield: 6.9 g (91.5%); m.p. 280° C. dec.; $[\alpha]_D^{20} -6.8°$ (c=0.5, TFE).

Anal.: Calc. for $C_{185}H_{321}N_{27}O_{53}$ (3771.74): C 58.91, H 8.58, N 10.03; Found: C 58.72, H 8.65, N 9.86.

(h)
Ac-Ser(tBu)-Asp(OtBu)-Ala-Ala-Val-Asp(OtBu)-Thr(tBu)-Ser(tBu)-Ser(tBu)-Glu(OtBu)-Ile-Thr(tBu)-Thr(tBu)-Lys(Boc)-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn-OtBu

A solution of Z-Thr(tBu)-Ser(tBu)-Ser(tBu)-Glu(OtBu)-Ile-Thr(tBu)-Thr(tBu)-Lys(Boc)-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn-OtBu (1.2 g, 0.32 mmol) in 30 ml TFE was hydrogenated in the presence of 10% Pd-C. The reaction mixture was filtered through dicalite and evaporated in vacuo. The residue was taken up in about 50 ml $CHCl_3$ and Ac-Ser(tBu)-Asp(OtBu)-Ala-Ala-Val-Asp(OtBu)-OH (0.5 g, 0.64 mmol), HOBt (173 mg, 1.28 mmol) were added. The mixture was stirred for about 1 h at 25° C. before DCC (158 mg, 0.77 mmol) was added. Stirring was continued for 24 h at 25° C. before the gelatinous reaction mixture was poured into hexane. The resulting precipitate was filtered off, washed with 5% $NaHCO_3$ sol. and $H_2O$ and triturated with hot ethanol and methanol and dried in vacuo.

Yield: 1.2 g (85%); m.p. ~300° C.

Anal.: Calc. for $C_{213}H_{375}N_{33}O_{63}$ (4406.51): C 58.06, H 8.58, N 10.49; Found: C 57.71, H 8.59, N 10.30.

In a separate experiment a solution of Z-Thr(tBu)-Ser(tBu)-Ser(tBu)-Glu(OtBu)-Ile-Thr(tBu)-Thr(tBu)-Lys(Boc)-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn-OtBu (1.88 g, 0.5 mmol) in 30 ml TFE was hydrogenated in the presence of 10% Pd-C. The reaction mixture was filtered through dicalite and evaporated to dryness. The residue was triturated with a mixture of ethyl acetate-ether. The solid was filtered and dried in vacuo.

Yield: 1.6 g (88%); $[\alpha]_D^{20} -10°$ (c=0.5, TFE).

Anal.: Calc. for $C_{177}H_{315}N_{27}O_{51}$ (3637.61): C 58.44, H 8.73, N 10.40; Found: C 58.07, H 8.84, N 10.25.

(i)
Ac-Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn-OH (Thymosin$\alpha_1$)

For deprotection Ac-Ser(tBu)-Asp(OtBu)-Ala-Ala-Val-Asp(OtBu)-Thr(tBu)-Ser-(tBu)-Ser(tBu)-Glu(OtBu)-Ile-Thr(tBu)-Thr(tBu)-Lys(Boc)-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn(OtBu) (5.9 g, 1.34 mmol) was dissolved in a mixture of 120 ml TFA and 120 ml $CH_2Cl_2$ and stored under $N_2$ for 2.5 h at 25° C. The reaction mixture was poured into ether (2 l) and the resultant precipitate was filtered off and thoroughly washed with ether. The air-dried filter cake was dissolved in 0.2N acetic acid (300 ml), filtered and applied to a SP-Sephadex C-25 column (2.5×10 cm) previously equilibrated with 0.2N acetic acid. Elution was first carried out with 0.2N acetic acetic under UV-monitoring (207 nm) until all non-positively charged impurities were removed. The column was then washed with $H_2O$ before thymosin $\alpha_1$ was eluted with 0.1M ammonium acetate (pH 7). The thymosin $\alpha_1$ containing fractions were pooled and lyophilized to yield 3.8 g.

A 1.0 portion of the partially purified thymosin $\alpha_1$ was taken up in H$_2$O (30 ml) and the pH adjusted to 6.5 (3% NH$_4$OH), filtered through a 0.45$\mu$ Millipore filter and applied on to an ODS-3 Magnum M20 HPLC-column (2×50 cm) previously equilibrated with 0.02M ammonium acetate buffer (pH 4.75). The column is washed with the same buffer at a flow rate of 8 ml/min. for 1 h. Elution of thymosin $\alpha_1$ was carried out isokratically with acetonitril-0.02M ammonium acetate pH 4.75 (13–87 v/v) at the same flow rate using UV-monitoring at 212–216 nm. The eluate of the first 2 h (960 ml) is discarded, then 8 ml fractions are collected over a 3 h period. Aliquots of representative fractions are analysed for their content of thymosin $\alpha_1$ and impurities by analytical HPLC on a reverse phase column (C$_{18}$) in the system: acetonitril-0.025% trifluoroacetic acid (18.5–81.5 v/v). Appropriate fractions were pooled, partially evaporated and lyophilized to yield after repetitive relyophilizations from dilute NH$_4$OH 320 mg of highly purified thymosin $\alpha_1$. Amino acid analysis: (6M HCl, 110° 24 and 72 h) Lys (4.02); Asp (4.00); Thr (3.07); Ser (3.00), Glu (6.03); Ala (3.03); Val (3.02); Ile (1.02); Leu (1.03).

We claim:
1. A compound of the formula Z-Thr(tBu)-Ser(tBu)-Ser(tBu)-Glu(OtBu)-Ile-Thr(tBu)-Thr(tBu)-Lys(Boc)-Asp(OtBu)-Leu-Lys(Boc)-Glu(OtBu)-Lys(Boc)-Lys(Boc)-GLu(OtBu)-Val-Val-Glu(OtBu)-Glu(OtBu)-Ala-Glu(OtBu)-Asn-OtBu, wherein Z is benzyloxycarbonyl, Boc is t-butyloxycarbonyl and tBu is t-butyl.
2. A compound of the formula H-Thr(tBu)-Ser(tBu)-Ser(tBu)-Glu(OtBu)-Ile-Thr(tBu)-Thr(tBu)-Lys(Boc)-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn-OtBu, wherein Boc is t-butyloxycarbonyl and tBu is t-butyl.

* * * * *